US007582737B2

United States Patent
Hung et al.

(10) Patent No.: US 7,582,737 B2
(45) Date of Patent: Sep. 1, 2009

(54) ORTHOGONALLY PROTECTED DISACCHARIDE BUILDING BLOCKS FOR SYNTHESIS OF HEPARIN OLIGOSACCHARIDES

(75) Inventors: Shang-Cheng Hung, Taipei (TW); Jing-Chyi Lee, Houbi Township, Tainan County (TW); Xin-An Lu, Tongluo Township, Miaoli County (TW)

(73) Assignee: Academia Sinica, Taipei (TW)

( * ) Notice: Subject to any disclaimer, the term of this patent is extended or adjusted under 35 U.S.C. 154(b) by 388 days.

(21) Appl. No.: 11/185,664

(22) Filed: Jul. 20, 2005

(65) Prior Publication Data

US 2006/0079483 A1 Apr. 13, 2006

Related U.S. Application Data

(60) Provisional application No. 60/589,496, filed on Jul. 20, 2004.

(51) Int. Cl.
C08B 37/10 (2006.01)
C13K 5/00 (2006.01)
C13K 7/00 (2006.01)
C07H 5/04 (2006.01)
C07H 5/06 (2006.01)
C08B 37/00 (2006.01)

(52) U.S. Cl. .................... 536/21; 536/123.13; 536/18.7

(58) Field of Classification Search .................... None
See application file for complete search history.

(56) References Cited

OTHER PUBLICATIONS

O'Neil et al. (eds.), The Merck Index, An Encyclopedia of Chemicals, Drugs, and Biologicals, 13th Editions, 2001, Merck & Co., Whitehouse Station, NJ, only pp. 830-831 supplied, see entry 4670 ("Heparin").*
Yu et al., "Novel Efficient Routes to Heparin Monosaccharides and Disaccharides Achived via Regio- and Stereoselective Glycosidation," Organic Letters, 6(5), 723-726 .(2004).*
Tabeur et al., "L-Iduronic Acid Derivatives as Glycosyl Donors," Carbohydrate Research, 281(2), 253-276 (1996); copy previously supplied by applicant.*
Noti et al., "Preparation and Use of Microarrays Containing Synthetic Heparin Oligosaccharides for the Rapid Analysis of Heparin-Protein Interactions," Chemistry: A European Journal, 12(34), 8664-8686 (2006).*
Lohman et al., "A Stereochemical Surprise at the Late Stage of the Synthesis of a Fully N-Differentiated Heparin Oligosaccharides Containing Amino, Acetamido, and N-Sulfonate Groups," Journal of Organic Chemistry, 69(12), 4081-4093 (2004).*
Yu et al., "Novel Efficient Routes to Heparin Monosaccharides and Disaccharides Achived via Regio- and Stereoselective Glycosidation," Organic Letters, 6(5), 723-726 .(2004).*
Hung et al., "Regioselective and Stereoselective Benzoylation of 2-N-Protected 4,6-O-Ketal Derivatives of D-Glucosamines with 1-(Benzoyloxy)benzotriazole," Carbohydrate Research, 330, 177-182 (2001): copy supplied by applicant.*
Tabeur et al., "L-iduronic acid derivatives as glycosyl donors," Carohydr. Res. 23;281(2):253-76.
Hirsh et al., "Guide to Anticoagulant Therapy: Heparin: A Statement for Healthcare Professionals From The American the American Heart Association," Circulation, Jun. 19, 2001;103(24):2994-3018.
Lee et al., "Synthesis of Heparin Oligosaccharides," J. Am Chem. Soc, 126:476-477 (2004) Publication Date Dec. 19, 2003, Plus Supplemental Information.

* cited by examiner

*Primary Examiner*—Lawrence E Crane
(74) *Attorney, Agent, or Firm*—Hsiu-Ming Saunders; Intellectual Property Connections, Inc.

(57) ABSTRACT

Orthogonally protected disaccharide building blocks for synthesis of heparin oligosaccharide. The disaccharide building block has a formula (I), in which L is a leaving group, $P^1$, $P^2$, $P^3$ and are different, and of them $P^1$ is an ester-type protecting group, $P^2$ is a hydroxyl protecting group that could be oxidized to a carboxylic acid, $P^3$ is a hydroxyl protecting group, and $P^4$ is a hydroxyl protecting group which allows chemoslective deprotection with 2,3-dichloro-5,6-dicyano-1,4-benzoquinone (DDQ). Acting as an elongation unit, the disaccharide building block of formula (I) may react with a starting unit of formula (II) to synthesize a heparin oligosaccharide.

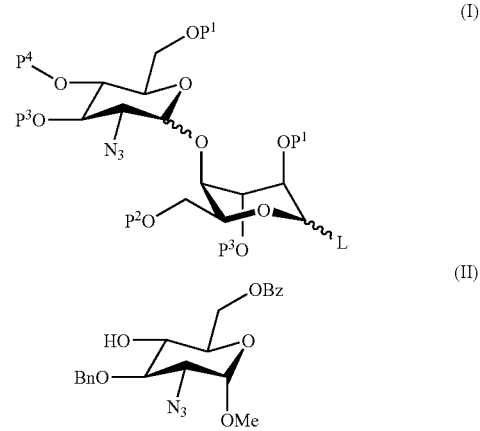

20 Claims, 2 Drawing Sheets

ORTHOGONALLY PROTECTED DISACCHARIDE BUILDING BLOCKS FOR SYNTHESIS OF HEPARIN OLIGOSACCHARIDES

The present application claims priority to U.S. Provisional Application Ser. No. 60/589,496, filed Jul. 20, 2004, herein incorporated by reference in its entirety.

FIELD OF THE INVENTION

The present invention relates to composition and methods for the synthesis of low molecular weight heparins and heparinoids. The present invention also relates to compositions having substantially homogenous populations of desired heparin molecules, or molecules useful in the synthesis of heparin oligosaccharides.

BACKGROUND

Heparin and its structurally related heparan sulfate, the linear sulfated polysaccharides belonging to the family of glycosamino-glycans, play significant roles in a diverse set of biological processes, including blood coagulation, virus infection cell growth, inflammation, wound healing, tumor metastasis, lipid metabolism, and diseases of the nervous system. Heparin has a well-established utility as an anticoagulant drug and contains a trisulfated disaccharide repeating unit as the major component consisting of alternating D-glucosamine and L-iduronic acid with alpha 1→4 linkages:

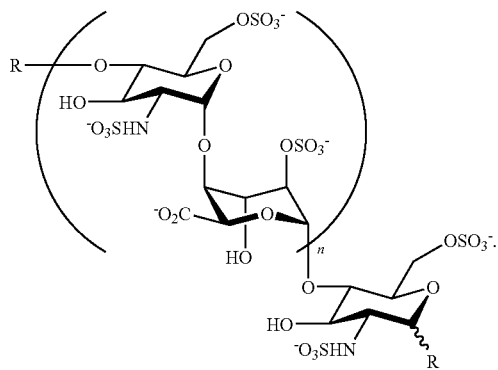

Enzymatic degradation of heparin with heparinase gives a mixture of oligosaccharides with even sugar units invariably having an unsaturated D-glucuronic acid residue at the non-reducing end:

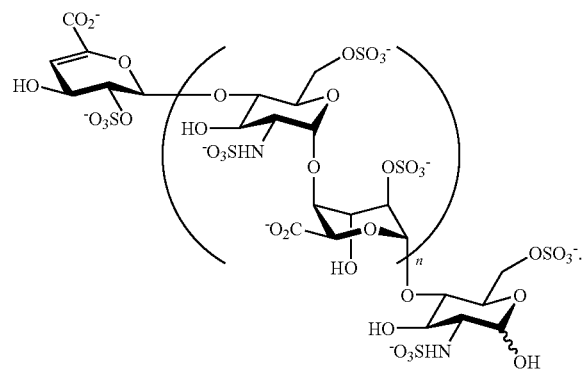

Low molecular weight heparins and heparinoids such as fondaparinux sodium (ARIXTRA), methyl O-2-deoxy-6-O-sulfo-2-(sulfoamino)-alpha-D-glucopyranosyl-(1→4)-O-beta-D-glucopyranuronosyl-(1→4)-O-2-deoxy-3,6-di-O-sulfo-2-(sulfoamino)-alpha-D-glucopyranosyl-(1→4)-O-2-O-sulfo-alpha-L-idopyranuronosyl-(1→4)-2-dexoy-6-O-sulfo-2-(sulfoamino)-alpha-D-glucopyranoside, decasodium salt and tinzaparin sodium (INNOHEP):

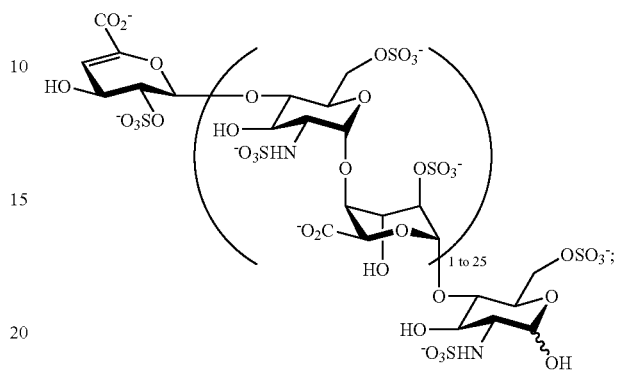

are FDA approved antithrombotics with well-known utilities for the prevention of blood clotting. Tinzaparin sodium is obtained by controlled enzymatic depolymerization of heparin from porcine intestinal mucosa using heparinase from *Flavobacterium heparinum* resulting in molecular weight distributions from <2,000 daltons to >8,000 daltons. Similarly, low molecular weight heparins and heparinoids including dalteparin, enoxaparin, ardeparin, certoparin, nadroparin, pamaparin, and reviparin are obtained by depolymerization methods of mucosa resulting in compositions having various molecular weight distributions.

Low molecular weight heparins of varying molecular weights can have substantial therapeutic implications, such as undesirable side effects. It is well known that producing therapeutics with more homogeneous compositions can decrease side effects. For example, current low molecular weight heparins and heparinoids when concurrently used with spinal epidural anesthesia, or spinal puncture may cause bleeding or hematomas (collection of blood) within the spinal column. When bleeding occurs in the spinal column, increased pressure on the spinal cord may result in permanent paralysis. The exact reason for this occurrence is not understood; however, it is hypothesized to be the side effect of one or more of undesirable low molecular weight heparin or heparinoid compositions or conformations. Thus, there is a need for improved methods of obtaining low molecular weight heparins polymers that are substantially pure and have homogeneous structural configurations, confirmations, and stereomeric compositions.

The frequently encountered problems in the synthesis of polymeric heparin molecules with substantially homogeneous compositions include the generation of rare L-idose, the differentiation of the isomeric configuration of hydroxyl groups on each sugar residue, stereocontrol in the construction of alpha and beta-glycosidic bonds, the cleavage of multi-protecting groups, and the transformation of multi-functional groups. Thus, there is a need for synthetic methods of producing low molecular weight heparins and heparinoid that reduce the efforts for the generation of L-idose, allow the cleavage of multiple protecting groups, differentiation of hydroxyl groups on the sugar residues and allow for the control of the construction of alpha and beta-glycosidic bonds.

SUMMARY OF THE INVENTION

The present invention provides composition and methods for the synthesis of low molecular weight heparins and heparinoids (e.g., useful as antithrombotics). The present invention also provides compositions having substantially homogenous populations of desired heparin molecules, or molecules useful in the synthesis of heparin oligosaccharides.

In some embodiments, the present invention provides a compound comprising the following formula:

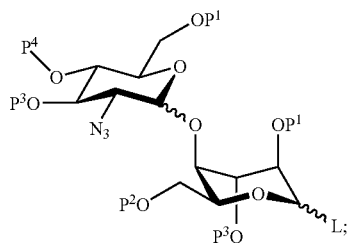

wherein L is alkoxy or trichloroacetimidate; $P^1$ is a hydrogen, benzoyl or substituted benzoyl; $P^2$ is a hydrogen, alkylcarbonyl, or substituted alkylcarbonyl; $P^3$ is a benzyl or substituted benzyl; and $P^4$ is hydrogen, 2-naphthylmethyl, substituted 2-naphthylmethyl, p-methoxybenzyloxymethyl, substituted p-methoxybenzyloxymethyl, p-methoxybenzyl, or substituted p-methoxybenzyl.

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% of the alpha-linked isomer of the above compound. In additional embodiments, the compound component comprises greater than 55%, or greater than 80% or 90% of the beta-linked isomer of the above compound.

In other embodiments, the present invention provides a compound comprising the following formula:

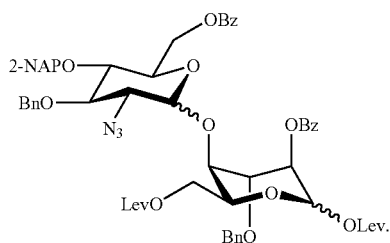

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% (e.g., about 95%) of the alpha-linked isomer of the above compound (e.g., about 95% of all the molecules in the composition that fall within the formula given above are the alpha-linked isomer). In additional embodiments, the compound component comprises greater than 55%, or greater than 80% or 90% (e.g., about 95%) of the beta-linked isomer of the above compound.

In some embodiments, the present invention provides a compound comprising the following formula:

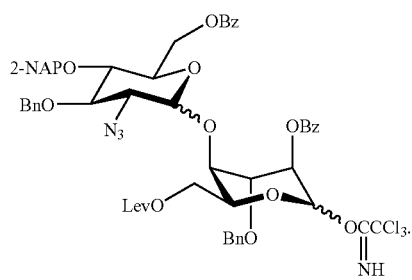

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% of the alpha-linked isomer of the above compound. In additional embodiments, the compound component comprises greater than 55%, or greater than 80% or 90% of the beta-linked isomer of the above compound. In other embodiments, any of the compositions disclosed herein comprise an excipient component.

In some embodiments, the present invention provides a compound having the following formula:

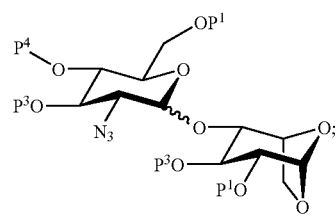

wherein $P^1$ is a benzoyl, or substituted benzoyl; $P^3$ is a benzyl or substituted benzyl; and $P^4$ is hydrogen, 2-naphthylmethyl, substituted 2-naphthylmethyl, p-methoxybenzyloxymethyl, substituted p-methoxybenzyloxymethyl, p-methoxybenzyl, or substituted p-methoxybenzyl.

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% of the alpha-linked isomer of the above compound. In additional embodiments, the compound component comprises greater than 55%, or greater than 80% or 90% of the beta-linked isomer of the above compound.

In some embodiments, the present invention provides a compound with the following formula:

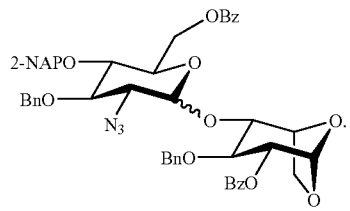

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% of the alpha-linked isomer of the above compound. In additional embodiments, the compound component comprises greater than 55%, or greater than 80% or 90% of the beta-linked isomer of the above compound.

In some embodiments, the present invention provides compounds with the following formula:

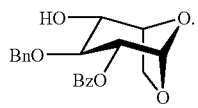

In other embodiments, the present invention provides compounds with the following formula:

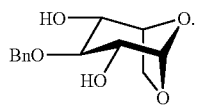

In certain embodiments, the present invention provides compositions with the following formula:

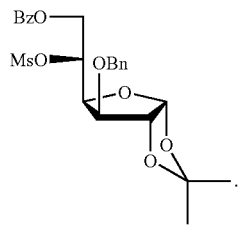

In some embodiments, the present invention provides compounds with the following formula:

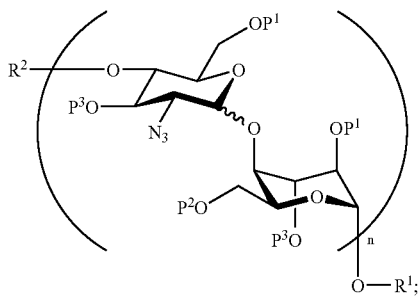

wherein n is 1 to 1000; $R^1$ is a alkyl, substituted alkyl, saccharide, polysaccharide, or

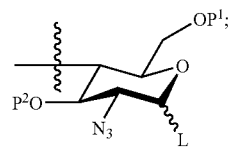

L is alkoxy or trichloroacetimidate; $P^1$ is a benzoyl; $P^2$ is an alkylcarbonyl or substituted alkylcarbonyl; $P^3$ is a benzyl; and $R^2$ is a hydrogen, alkyl, substituted alkyl, 2-O-sulpho-4-enepyranosuronic acid, 2-naphthylmethyl, substituted 2-naphthylmethyl, p-methoxybenzyloxymethyl, substituted p-methoxybenzyloxymethyl, p-methoxybenzyl, substituted p-methoxybenzyl, saccharide or polysaccharide.

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% of the all alpha-linked isomer of the above compound. In additional embodiments, the compound component comprises greater than 55%, or greater than 80% or 90% of the all beta-linked isomer of the above compound.

In certain embodiments, the present invention provides compositions comprising a heparin component, wherein the heparin component is composed of all the heparin or heparinoid molecules present in the composition. In some embodiments, the heparin component comprises greater than 55%, or greater than 80% or 90% of the above compound. In additional embodiments, the present invention provides compositions consisting essentially of the above compound.

In some embodiments, the present invention provides a compound with the formula:

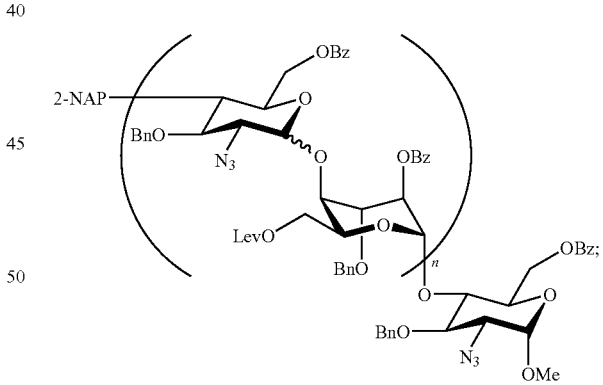

wherein n is 1 to 1000.

In particular embodiments, the present invention provides compositions comprising a compound component, wherein the compound component is composed of all the molecules of the above compound present in the composition. In certain embodiments, the compound component comprises greater than 55%, or greater than 65%, 75%, 80% or 90% of the all alpha-linked isomer of the above compound. In additional embodiments, the compound component comprises greater than 55%, or greater than 80% or 90% of the all beta-linked isomer of the above compound.

In some embodiments, the present invention provides compounds with the following formula:

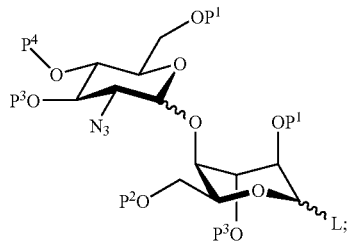

wherein L is a leaving group for creating a chemical bond between the adjoining methane carbon and the oxygen of an alcohol; $P^1$ is a leaving group for preventing modification of the adjoining oxygen and exposing a hydroxyl group in a solution consisting essentially of the compound and sodium methoxide at room temperature; $P^2$ is a leaving group for preventing modification of the adjoining oxygen and exposing a hydroxyl group in a solution consisting essentially of the compound and hydrazine at room temperature; $P^3$ is a leaving group for preventing modification of the adjoining oxygen and exposing a hydroxyl group in a solution consisting essentially of the compound, hydrogen gas, and 10% Pd/C when under 50 psi pressure of hydrogen gas at room temperature; $P^4$ is a leaving group for preventing modification of the adjoining oxygen and exposing a hydroxyl group in a solution consisting essentially of either 1) the compound, hydrogen gas, and 10% Pd/C when under 50 psi pressure of hydrogen gas at room temperature or 2) the compound and 2,3-dichloro-5,6-dicyano-1,4-benzoquinone at room temperature.

In certain embodiments, the present invention provides compositions comprising a heparin component, wherein the heparin component is composed of all the heparin or heparinoid molecules present in the composition. In some embodiments, the heparin component comprises greater than 55%, or greater than 65%, 75%, 80% or 90% of the above compound. In additional embodiments, the present invention provides compositions consisting essentially of the above compound.

In certain embodiments, the present invention provides compounds having the following formula:

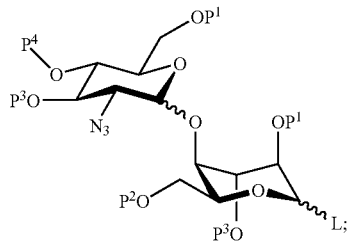

wherein L is a leaving group for creating a chemical bond between the adjoining methane carbon and the oxygen of an alcohol; $P^1$ is a leaving group for preventing modification of the adjoining oxygen and exposing a hydroxyl group in a solution consisting essentially of the compound and sodium methoxide at room temperature; $P^2$ is a leaving group for preventing modification of the adjoining oxygen and exposing a hydroxyl group in a solution consisting essentially of the compound and hydrazine at room temperature; $P^3$ is a leaving group for preventing modification of the adjoining oxygen and exposing a hydroxyl group in a solution consisting essentially of the compound, hydrogen gas, and 10% Pd/C when under 50 psi pressure of hydrogen gas at room temperature; $P^4$ is a leaving group for preventing modification of the adjoining oxygen and exposing a hydroxyl group in a solution consisting essentially of either 1) the compound, hydrogen gas, and 10% Pd/C when under 50 psi pressure of hydrogen gas at room temperature or 2) the compound and 2,3-dichloro-5,6-dicyano-1,4-benzoquinone at room temperature.

In some embodiments, the present invention provides compounds with the following formula:

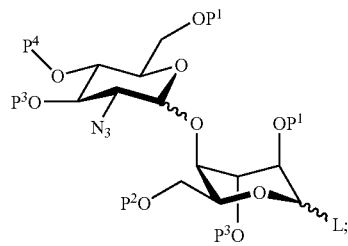

wherein L is an agent for creating a chemical bond between the adjoining methane carbon and the oxygen of an alcohol; $P^1$ is an agent for preventing modification of the adjoining oxygen and exposing a hydroxyl group in a solution comprising the compound and sodium methoxide at room temperature; $P^2$ is an agent for preventing modification of the adjoining oxygen and exposing a hydroxyl group in a solution comprising the compound and hydrazine at room temperature; $P^3$ is an agent for preventing modification of the adjoining oxygen and exposing a hydroxyl group in a solution comprising the compound, hydrogen gas, and 10% Pd/C when under 50 psi pressure of hydrogen gas at room temperature; $P^4$ is an agent for preventing modification of the adjoining oxygen and exposing a hydroxyl group in a solution comprising either 1) the compound, hydrogen gas, and 10% Pd/C when under 50 psi pressure of hydrogen gas at room temperature or 2) the compound and 2,3-dichloro-5,6-dicyano-1,4-benzoquinone at room temperature.

In certain embodiments, the present invention provides compositions comprising a heparin component, wherein the heparin component is composed of all the heparin or heparinoid molecules present in the composition. In some embodiments, the composition comprises a heparin component comprising greater than 80%, or greater than 90%, 95% or 99% of a heparin compound with the following formula:

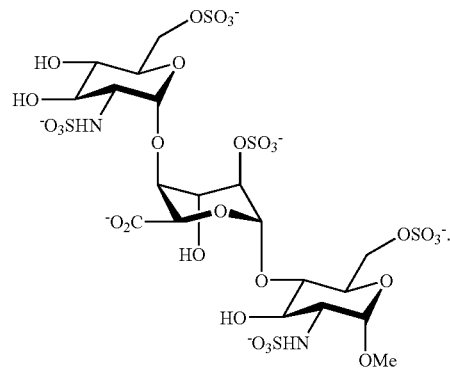

In additional embodiments, the present invention provides compositions consisting essentially of the above compound.

In other embodiments, the composition comprises a heparin component comprising greater than 80%, or greater than 90%, 95% or 99% of a heparin compound with the following formula:

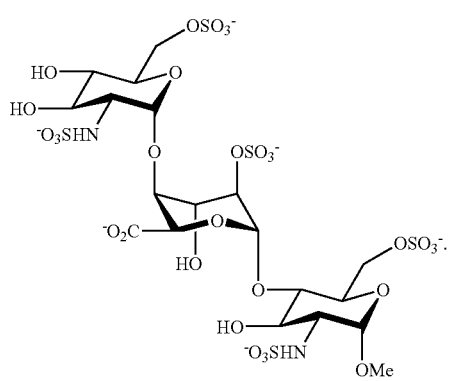

In particular embodiments, the composition comprises a heparin component comprising greater than 80%, or greater than 90%, 95% or 99% of a heparin compound with the following formula:

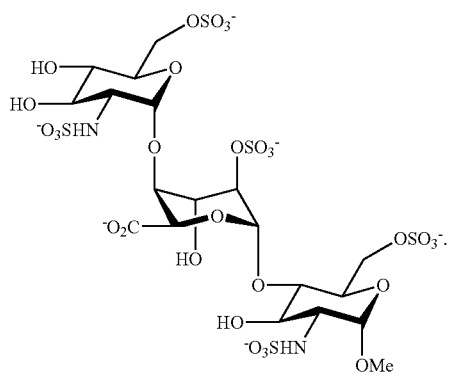

In additional embodiments, the composition comprises a heparin component comprising greater than 80%, or greater than 90%, 95% or 99% of a heparin compound with the following formula:

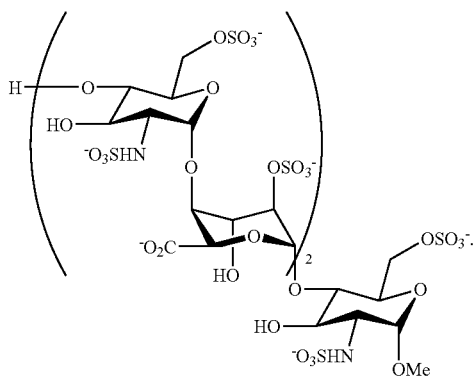

In other embodiments, the composition comprises a heparin component comprising greater than 80%, or greater than 90%, 95% or 99% of a heparin compound with the following formula:

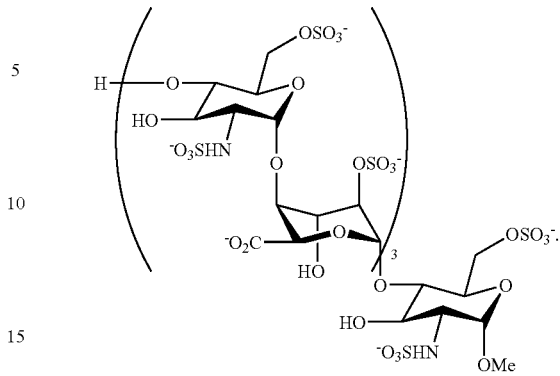

In additional embodiments, the composition comprises a heparin component comprising greater than 80%, or greater than 90%, 95% or 99% of a heparin compound with the following formula:

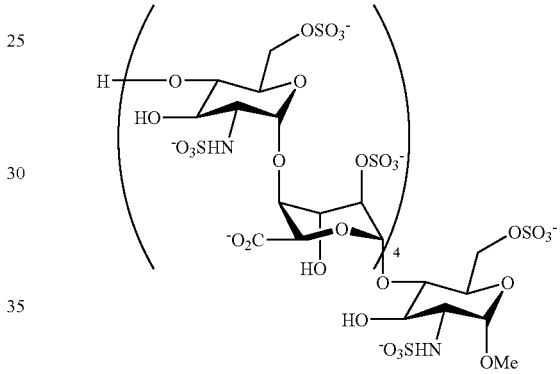

In particular embodiments, the present invention provides compositions comprising a compound component, wherein the compound component is composed of all the molecules present in the composition with the following formula:

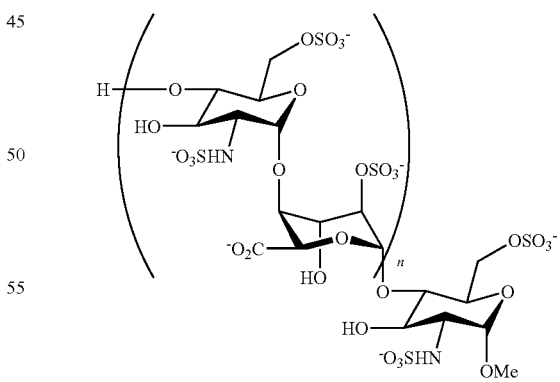

wherein n is 2 to 25. In certain embodiments, the compound component comprises greater than 65% or 75% of the alpha-linked isomer of the above compound.

In particular embodiments, the present invention provides compositions comprising a compound component, wherein the compound component is composed of all the molecules present in the composition with the following formula:

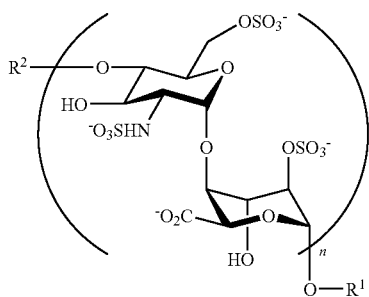

wherein n is 2 to 50; wherein $R^1$ is hydrogen, alkyl, substituted alkyl, saccharide, or substituted saccharide and wherein $R^2$ is hydrogen, alkyl, substituted alkyl, saccharide, or substituted saccharide. In certain embodiments, the compound component comprises greater than 75% of the all alpha-linked isomer of the above compound.

In some embodiments, the present invention provides methods of making a first compound of the formula:

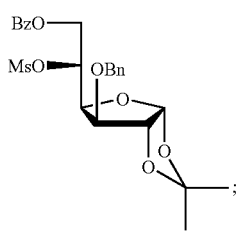

comprising a) providing a second compound of the formula:

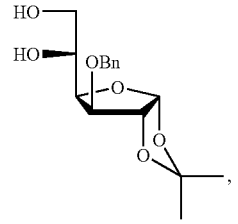

benzoyl chloride, and methanesulfonyl chloride; b) mixing the second compound, benzoyl chloride, and methanesulfonyl chloride under conditions such that the first compound is generated.

In other embodiments, the present invention provides methods of making a first compound of the formula:

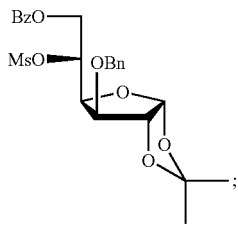

comprising a) providing a second compound of the formula:

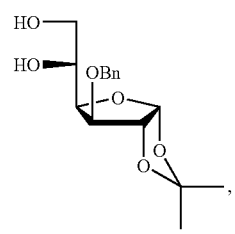

benzoyl chloride, methanesulfonyl chloride, and a coupling catalyst (e.g. preferably pyridine); b) mixing the second compound, coupling catalyst, benzoyl chloride, and methanesulfonyl chloride under conditions such that the first compound is generated.

Another embodiment is a method of making a first compound of the formula:

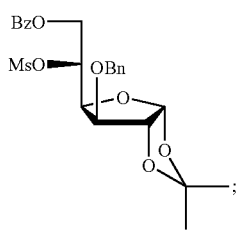

comprising a) providing a second compound of the formula:

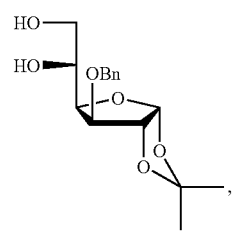

benzoyl chloride, methanesulfonyl chloride, and a coupling catalyst (e.g., preferably pyridine); b) mixing the second compound and coupling catalyst, and c) adding to the mixture benzoyl chloride and methanesulfonyl chloride under conditions such that the first compound is generated.

In other embodiments, the present invention provides methods of making a first compound of the formula:

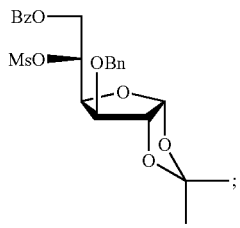

comprising a) providing a second compound of the formula:

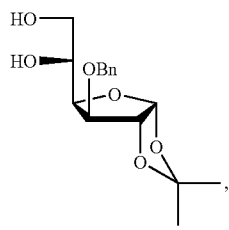

benzoyl chloride, methanesulfonyl chloride, and a coupling catalyst preferably pyridine; b) mixing the second compound, and the coupling catalyst; c) cooling the second compound and the coupling catalyst mixture to at least about 0° C.; and d) adding to the mixture benzoyl chloride and methanesulfonyl chloride under conditions such that the first compound is generated.

In certain embodiments, the present invention provides methods of making a first compound with the formula:

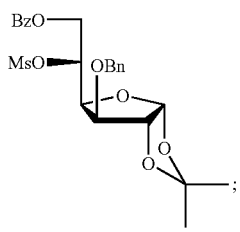

comprising a) providing a second compound of the formula:

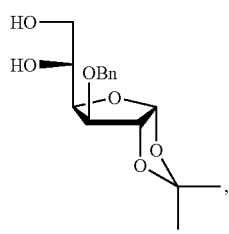

benzoyl chloride, methanesulfonyl chloride, and a coupling catalyst preferably pyridine; b) mixing the second compound and the coupling catalyst; c) cooling the second compound, and pyridine mixture to 0° C.; d) adding to the mixture benzoyl chloride before adding the methanesulfonyl chloride, and e) adding the methanesulfonyl chloride under conditions such that the first compound is generated.

In some embodiments, the present invention provides methods of making a first compound with the formula:

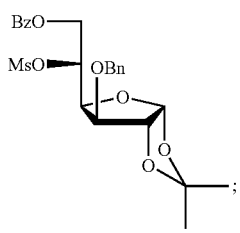

comprising a) providing a second compound of the formula:

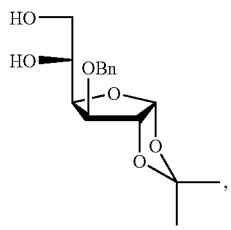

benzoyl chloride, methanesulfonyl chloride, and coupling catalyst (e.g., preferably pyridine); b) mixing the second compound:

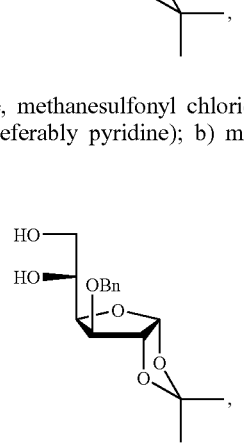

and coupling catalyst; c) cooling the second compound and coupling catalyst mixture to about 0° C.; d) adding benzoyl chloride to the mixture before adding methanesulfonyl chloride; e) adding methanesulfonyl chloride to the mixture, and f) isolating the first compound (e.g. in substantially pure form).

In some embodiments, the present invention provides methods of making a first compound with the following formula:

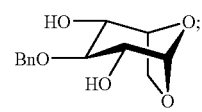

comprising a) providing a basic composition (e.g. preferably potassium t-butoxide), a solvent preferably tert-butyl alcohol and methylene chloride, a high temperature boiling solvent (e.g. preferably diglyme), and a second compound of the formula:

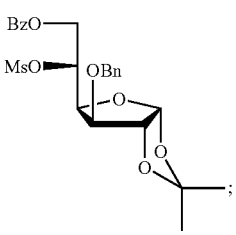

b) mixing the solvent and the second compound, c) cooling the mixture of the solvent and the second compound to 0° C.; d) adding the basic composition to the mixture, e) adding the high temperature boiling solvent to the mixture, and f) heating the mixture to a temperature >100° C. in order to generate the first compound.

Another embodiment is a method of making a first compound of the formula:

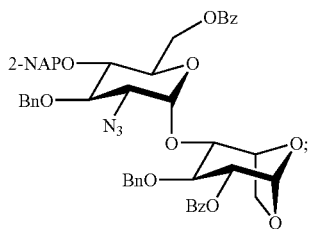

comprising a) providing a basic compound (e.g. preferably potassium carbonate), a solvent (e.g. preferably methylene chloride), a leaving group reagent (e.g., preferably trichloroacetonitrile), a coupling catalyst (e.g., preferably trimethylsilyl trifluoromethanesulfonate), a second compound of the formula:

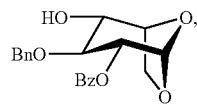

and a third compound of the formula:

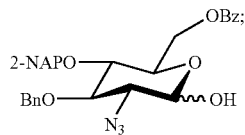

b) mixing the solvent and the third compound; c) cooling the mixture of the solvent and the third compound to a temperature below 0° C. (e.g. preferably below −75° C.); d) adding the leaving group reagent to the mixture; e) removing substantially any excess leaving group reagent; f) adding the second compound to the mixture; and g) adding the coupling catalyst under conditions such that the first compound is generated.

Another embodiment is a method of making a first compound of the formula:

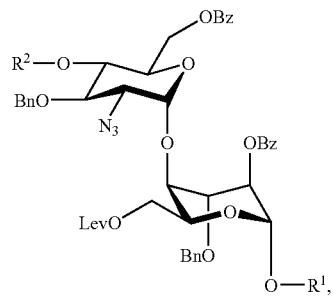

wherein $R^2$ is a hydrogen, alkyl, substituted alkyl, 2-O-sulpho-4-enepyranosuronic acid, 2-naphthylmethyl, substituted 2-naphthylmethyl, p-methoxybenzyloxymethyl, substituted p-methoxybenzyloxymethyl, p-methoxybenzyl, substituted p-methoxybenzyl, saccharide or polysaccharide and wherein $R^1$ is an alkyl, substituted alkyl, saccharide, or polysaccharide; comprising a) providing a basic compound (e.g. preferably potassium carbonate), a solvent (e.g. preferably methylene chloride), a leaving group reagent (e.g., preferably trichloroacetonitrile), and a coupling catalyst (e.g. preferably trimethylsilyl trifluoromethanesulfonate), a second compound of the formula: $R^1$—OH, and a third compound of the formula:

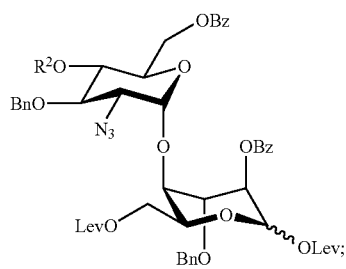

b) mixing the solvent and the third compound; c) cooling the mixture of the solvent and the third compound to a temperature below 0° C. (e.g., preferably below −75° C.); d) adding the leaving group reagent to the mixture; e) removing substantially any excess first leaving group reagent from the mixture; f) adding the second compound to the mixture; and g) adding the coupling catalyst under conditions such that the first compound is generated.

In some embodiments, the present invention provides methods of treating a subject comprising; a) providing, i) a subject; and ii) a composition comprising one or more of the heparin or heparinoid compounds described above; and b) administering the composition to the subject. In certain embodiments, the composition is administered as an antithrombotic. In particular embodiments, the subject has a disease and the administering reduces or eliminates at least one symptom of the disease.

DEFINITIONS

Figure 1:
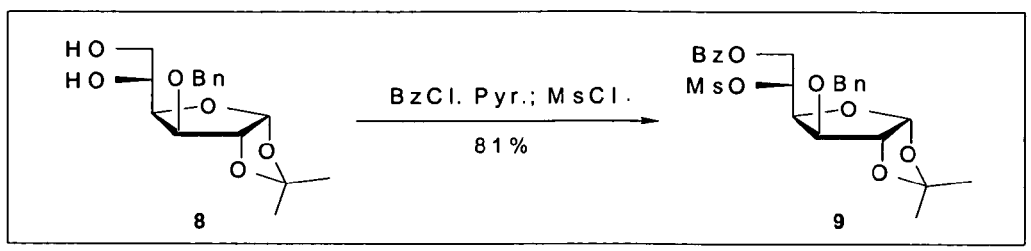
FIGS. 1A, 1B, 1C and 1D show synthesis schemes from Examples 1-4.
Figure 1:
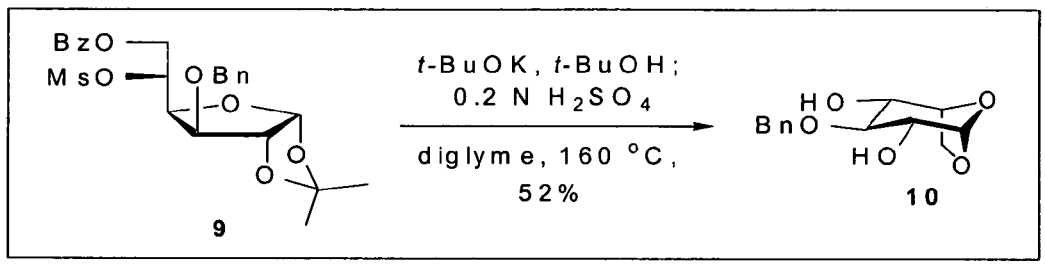
Figure 1:
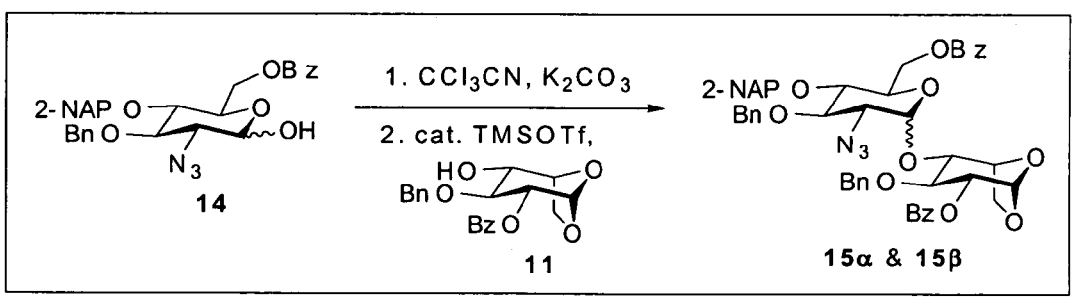
Figure 1:
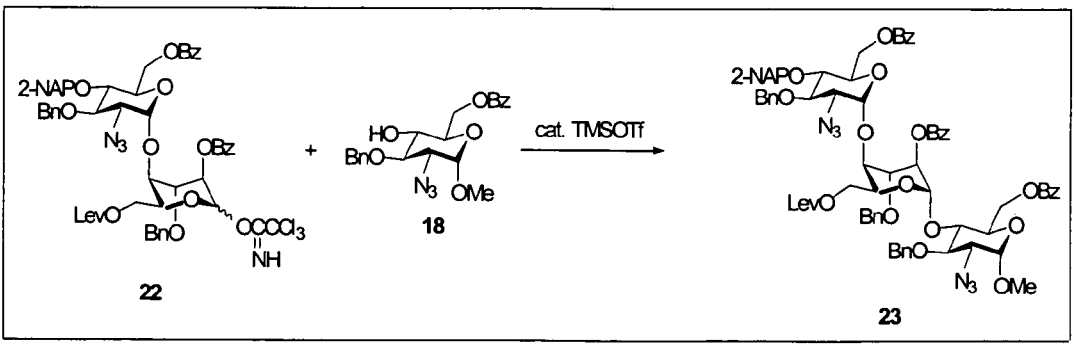

"Adjoining" atoms means atoms that are chemically bonded to each other.

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkoxy" means an alkyl moiety attached through an oxygen bridge (i.e., —O-alkyl) such as methoxy, ethoxy, and the like.

"Alkycarbonyl" means an alkyl moiety attached through an carbonyl bridge (i.e., —C(=O)-alkyl) such as acetyl and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —$SO_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

"Alpha-linked isomer" means a sugar attached through an oxygen bridge to another sugar such that the oxygen of the oxygen bridge on the first carbon and the methylene on the fifth carbon have a trans confirmation:

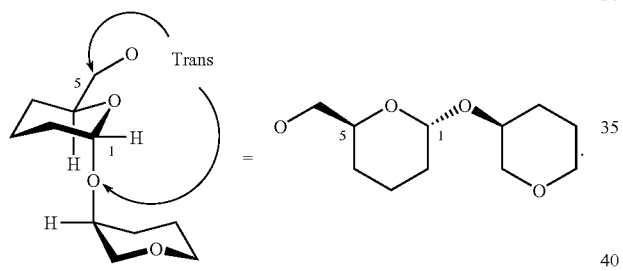

"Aryl" means an aromatic carbocyclic moiety such as phenyl or naphthyl.

"Arylalkyl" means an alkyl having at least one alkyl hydrogen atoms replaced with an aryl moiety, such as benzyl, —$(CH_2)_2$phenyl, —$(CH_2)_3$phenyl, —CH(phenyl)$_2$, and the like.

"Beta-linked isomer" means a sugar attached through an oxygen bridge to another sugar such that the oxygen of the oxygen bridge on the first carbon and the methylene on the fifth carbon has a cis confirmation:

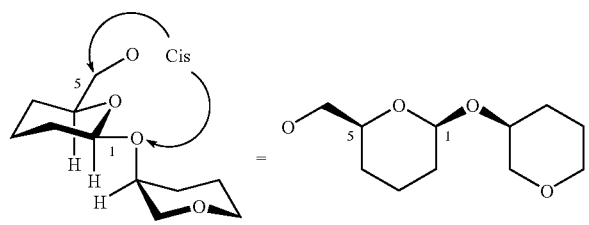

A "coupling catalyst" means a molecular entity that temporarily interacts with a molecule after displacing a leaving group until the entity is itself displaced by a nucleophile. For example, pyridine or dimethylamino pyridine are routinely uses as carboxylic acid coupling catalyst because the pyridine reacts with activated carbonyls and is itself displaced by other nucleophiles (i.e., alcohols, amines, etc.)

"Exposing" or "deprotecting" a first atom, and the like, means breaking chemical bonds between the first atom and a second atom in a chemical structure intended to prevent modification of the first atom until exposure to a selected deprotecting reagent.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Halogen" means fluoro, chloro, bromo and iodo.

"Haloalkyl" means an alkyl having at least one hydrogen atom replaced with halogen, such as trifluoromethyl and the like.

"Heparin (or heparinoid)" compounds and the like means substituted or unsubstituted compounds of the following formula:

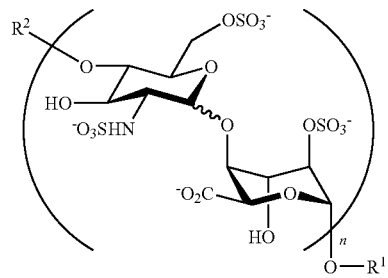

wherein n is at least one, $R^1$ is a alkyl, substituted alkyl, saccharide, substituted saccharide, polysaccharide, or substituted polysaccharide; and $R^2$ is a hydrogen, alkyl, substituted alkyl, 2-O-sulpho-4-enepyranosuronic acid, 2-naphthylmethyl, substituted 2-naphthylmethyl, p-methoxybenzyloxymethyl, substituted p-methoxybenzyloxymethyl, p-methoxybenzyl, substituted p-methoxybenzyl, saccharide, substituted saccharide, polysaccharide or substituted polysaccharide.

As used herein, the term "compound component" refers to that part of a composition that contains all of the molecules of a given compound, including all conformational and stereomeric forms. In preferred embodiments, a given isomer of a compound makes up a large percentage (e.g. by number of molecules and/or by weight) of the compound component. For example, an isomer of a certain compound may be present in an aqueous composition at a level where 70% of all the molecules of the compound are a particular isomer (e.g. alpha-linked isomer), while most of the composition itself is composed of water.

As used herein, the term "heparin component" refers to that part of a composition that contains all of the heparin or heparinoid molecules in a given composition, including all conformational and stereomeric forms. In preferred embodiments, a given compound (e.g. designated by a structure) makes up a large percentage (e.g. by number of molecules and/or by weight) of the heparin component. For example, a given heparin or heparinoid molecule may be present in an aqueous composition at a level where 70% of all the heparin or heparinoid molecules are of that given compound, while most of the composition itself is composed of water.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

A "leaving group" means a molecular arrangement that creates higher relative reactivity by shifting electron density away from a reactive site causing nucleophiles to bond with the reactive site and break bonds with the leaving group. For example, the chlorine of an acid chloride shifts electron density away from the carbon of the carbonyl group increasing the carbonyl's carbon reactivity to alcohols that will form bonds between the oxygen and the carbonyl's carbon and break the bond with the chlorine. There are many leaving groups known to those skilled in the art.

A "leaving group reagent" means a reagent used with the intent to introduce leaving groups into molecules.

"Modification" of an atom means adding a new chemically bonded atom to said atom, eliminating the atom, and/or reducing or oxidizing the atomic hybridization state (i.e., sp$^2$ to an sp$^3$, reduction, or sp$^3$ to an sp, oxidation).

A "nucleophile" (or nucleophilic reagent) is a reagent that forms a bond to its reaction partner by donating bonding electrons.

"Polysaccharide" means a compound that consists of two or more saccharide residues.

"Saccharide" means a sugar (i.e., compounds having a large ratio of primary and secondary protected or unprotected hydroxyl groups).

The term "substituted" as used herein means any of the above groups (i.e., alkyl, aryl, arylalkyl, heteroaryl, heteroarylalkyl, homocycle, heterocycle and/or heterocyclealkyl) wherein at least one hydrogen atom is replaced with a substituent. In the case of an oxo substituent ("=O"), two hydrogen atoms are replaced. When substituted one or more of the above groups are substituted, "substituents" within the context of this invention are halogen, hydroxyl, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. In addition, the above substituents may be further substituted with one or more of the above substituents, such that the substituent substituted alkyl, substituted aryl, substituted arylalkyl, substituted heterocycle or substituted heterocyclealkyl. R$_a$ and R$_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Methine carbon" means a carbon that is in an sp$^3$ hybridized state that is bonded to three other atoms and a single hydrogen atom.

DETAILED DESCRIPTION OF THE INVENTION

The present invention provides composition and methods for the synthesis of low molecular weight heparins and heparinoids (e.g. useful as antithrombotics). The present invention also provides compositions having substantially homogenous populations of desired heparin molecules, or molecules useful in the synthesis of heparin oligosaccharides.

This invention provides methods of preparing low molecular weight heparin and heparinoid compounds, which are polysaccharides having, for example, the following structures:

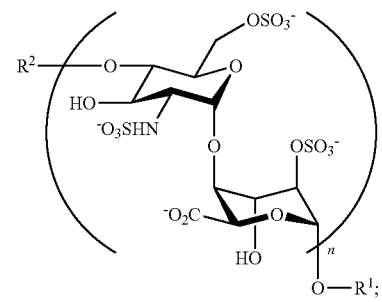

by elongation of a free hydroxyl group with an elongation disaccharide having the following formula:

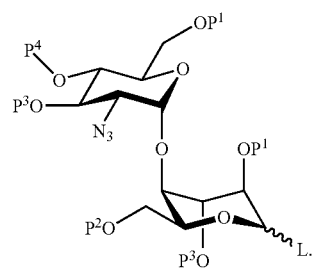

The 2-naphthylmethyl group (2-NAP), which is used to block the C4'-hydroxyl of the elongation disaccharide (P$^4$), allows chemoselective deprotection with 2,3-dichloro-5,6-dicyano-1,4-benzoquinone (DDQ) during chain-enhancement and simultaneous removal along with the permanent benzyl groups (P$^3$) in the final termination process. The ester protecting groups (P$^1$) not only offers anchimeric assistance (neighboring group participation) to generate 1,2-trans-glycosidic linkages, but also can be selectively removed to free those hydroxyls that ultimately carry sulfonate groups. In addition, a temporary protection (P²) is used to mask the primary hydroxyl on L-idose that could be oxidized to a carboxylic acid.

The elongation disaccharide may be produced using a L-idopyranosyl sugar:

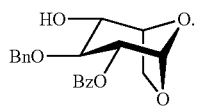

The L-idopyranosyl sugar is obtained from a 5,6-diol:

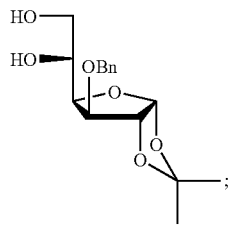

generated from, for example, commercially available diacetone alpha-D-glucose. The 5,6-diol may undergo one-pot benzoylation-mesylation to yield a furanose:

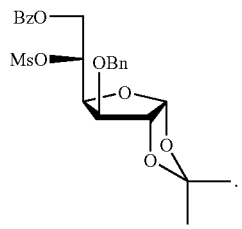

Treatment of the furanose with t-BuOK in t-BuOH followed by addition of a 1:2 mixture of 0.6 N H₂SO₄ and diglyme and subsequent heating at elevated temperature (160° C.) for 16 hours leads to the a 2,4-diol:

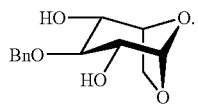

Regioselective benzoylation of the 2,4-diol provides a 2-ester

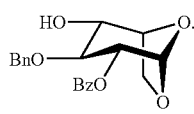

Glucosamine (D) hydrochloride may be first transformed into a 1,3-diol:;

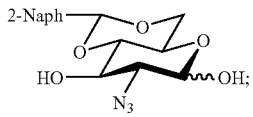

by employing a combination of amino-azido conversion at C2 and 4,6-O-naphthylidenation. Regioselective O1-benzoylation of the 1,3 diol: with 1-N-(benzyloxy)benzotriazole (BzOBT) followed by O3-benzylation affords a benzoyl and benzylated intermediate:

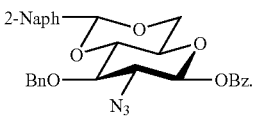

The benzoyl and benzylated intermediate may be subjected to sequential O6-ring opening, O6-benzoylation, and anomeric debenzoylation to provide a 1-alcohol:

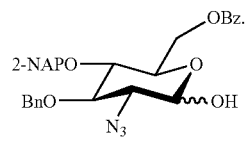

Transformation of the 1-alchol into the corresponding trichloroacetimidate and further coupling with the L-idopyranosyl sugar leads to a first alpha-linked disaccharide:

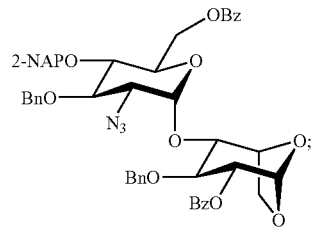

and a first beta-linked disaccharide:

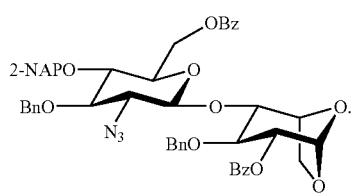

Cu(OTf)$_2$-catalyzed acetolysis of the first alpha-linked disaccharide delivers an alpha-linked 1,6-diacetate:

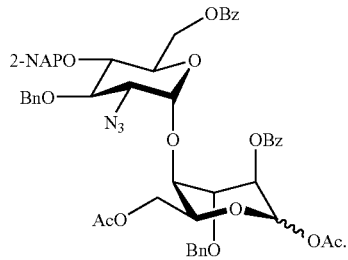

The use of the first beta-linked disaccharide results in a beta-linked 1,6-diacetate:

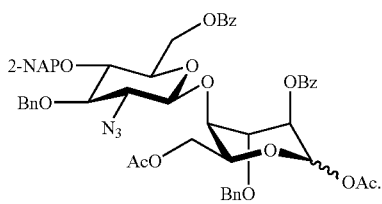

The alpha-linked 1,6-diacetate may be elective O1-deacetylated and converted to a first alpha-linked disaccharide trichloroacetimidate:

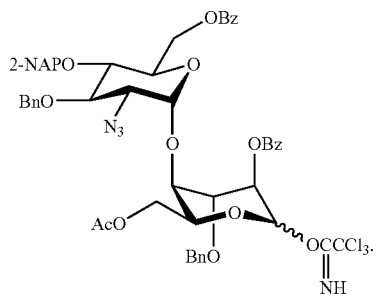

The beta-linked 1,6-diacetate results in a first beta-linked disaccharide trichloroacetimidate:

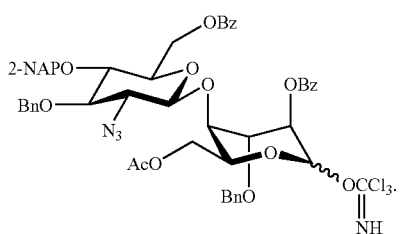

Methyl 2-azido-3-O-benzyl-2-deoxy-alpha-D-glucopyranoside may be prepared according to the procedures provide in Tebeur et al. Carohydr. Res. 1996, 281, 253 (herein incorporated by reference). Elective O6-benzoylation of methyl 2-azido-3-O-benzyl-2-deoxy-alpha-D-glucopyranoside provides a 4-alcohol, 2-azido-2-deoxy-3,6-O,O-dibenzyl-alpha-D-glucopyranoside:

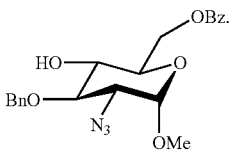

The 4-alcohol may be coupled with the alpha-linked disaccharide trichloroacetimidate to provide a first alpha, alpha-linked trisaccharide:

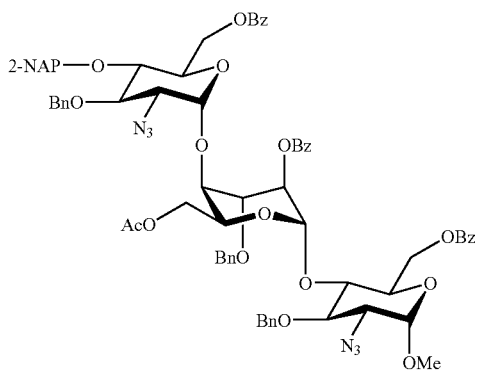

The 4-alcohol may be coupled with the beta-linked disaccharide trichloroacetimidate to provide a first alpha, beta-linked trisaccharide:

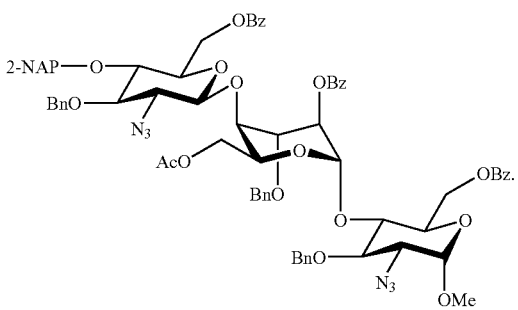

Further chain-elongation, involves removal of the O4-NAP using DDQ and subsequent glycosylation with the alpha-linked disaccharide trichloroacetimidate furnishing a first alpha, alpha, alpha, alpha-linked pentasaccharide:

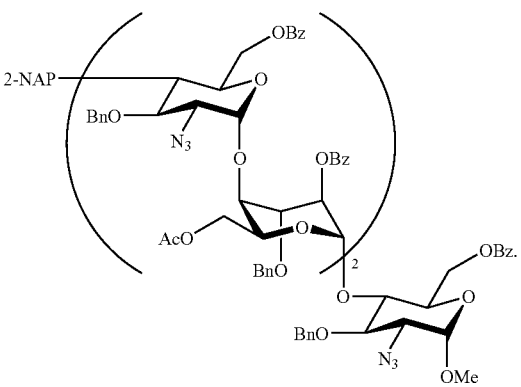

Deacetylation of the 1,6-diacetate affords a 1,6-diol, which may be reacted with Lev$_2$O in pyridine to get an alpha-linked 1,6-dilevulate:

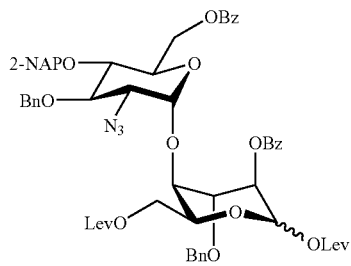

Similar reaction sequence of anomeric deprotection and imidate formation leads to a second alpha-linked disaccharide trichloroacetimidate:

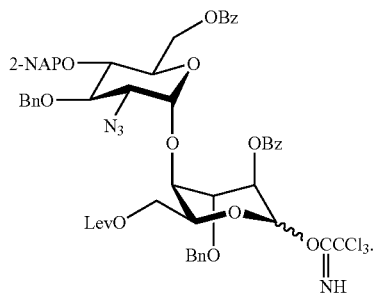

The second alpha-linked disaccharide trichloroacetimidate may be coupled with the previously described 4-alcohol in likewise manner to construct a second alpha, alpha-linked trisaccharide:

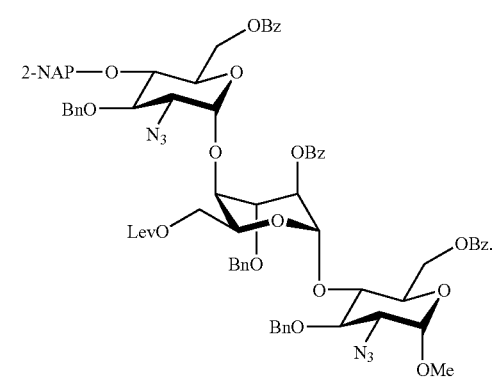

The elongation cycle may then be repeated multiple times to assemble polysaccharides. Cleavage of the Lev groups followed by oxidation using TEMPO, individually, furnishes acids:

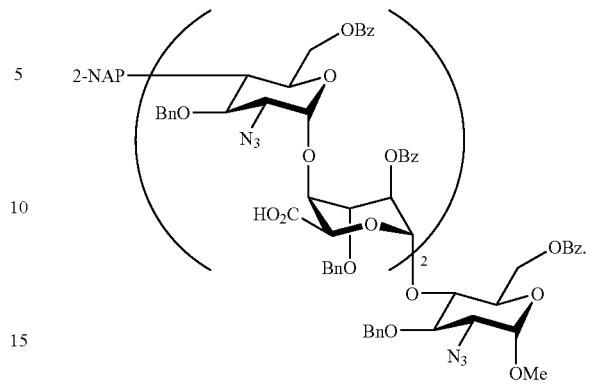

The Bz groups may be removed from the acids, followed by O-sulfonation, and hydrogenolysis reducing the OBn, O-2-NAP, and $N_3$ groups and subsequent N-sulfonation to provide the desired low molecular weight heparin derivatives:

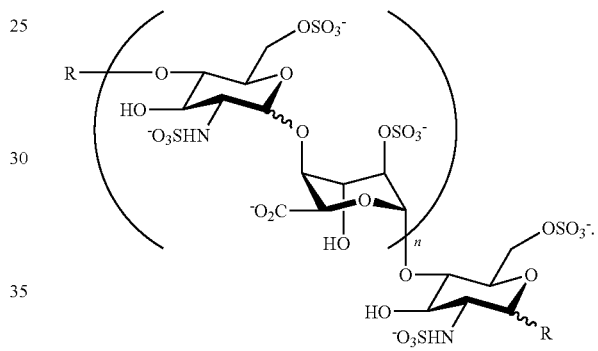

The heparin compositions of the present invention are useful for treating a subject with a disease. In preferred embodiments, the heparin compositions are administered to a patient with deep vein thrombosis, proximal venous thrombosis, clots in a patient, sepsis, or other conditions where heparin is generally useful (see, e.g., Hirsh et al., *Circulation,* 2001 June 19;103(24):2994-3018, herein incorporated by reference in its entirety for all purposes).

In some embodiments, the heparin or heparinoid molecules are conjugated to various radiolabels for both diagnostic and therapeutic purposes. Exemplary radiolabels include, but are not limited to, $^{131}$I, $^{125}$I, $^{123}$I, $^{99}$Tc, $^{67}$Ga, $^{111}$In, $^{188}$Re, $^{186}$Re, and preferably, $^{90}$Y. The heparin and heparinoid molecules of the present invention may also be administered in combination with other therapeutic moieties such as antibiotics or anti-thrombotic agents.

The heparin or heparinoid molecules of the present invention may be administered by any suitable means, including parenteral, non-parenteral, subcutaneous, topical, intraperitoneal, intrapulmonary, intranasal, and intralesional administration. Parenteral infusions include, but are not limited to, intramuscular, intravenous, intra-arterial, intraperitoneal, or subcutaneous administration.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. The dosages of the heparin or heparinoid molecules of the present invention are generally dependent on (a) the unique characteristics of the active compound and the particular therapeutic or prophylactic effect to be achieved, and (b) the limitations inherent in the art of compounding such an active compound for the treatment of sensitivity in individuals. Exemplary dosages are provided in Hirsh et al. (Circulation, 2001 Jun. 19; 103(24):2994-3018, herein incorporated by reference).

The dosage administered will, of course, vary depending upon known factors such as the pharmacodynamic characteristics of the particular agent, its mode and route of administration, the age, health, and weight of the recipient, the nature and extent of symptoms, the kind of concurrent treatment, the frequency of treatment, and the effect desired.

The heparin and heparinoid molecules of the invention can be incorporated into pharmaceutical compositions suitable for administration to a subject. For example, the pharmaceutical composition may comprise a heparin or heparinoid molecule and a pharmaceutically acceptable carrier. As used herein, "pharmaceutically acceptable carrier" includes solvents, dispersion media, coatings, antibacterial and antifungal agents, isotonic and absorption delaying agents, and the like that are physiologically compatible. Examples of pharmaceutically acceptable carriers include one or more of the following: water, saline, buffered saline solution, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the heparin or heparinoid molecules.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions.

Therapeutic compositions typically are sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by sterile filtration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson. ed., Marcel Dekker, Inc., New York, 1978).

In certain embodiments, the heparin or heparinoid molecules of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

EXAMPLES

It is to be understood that the examples are for purpose of illustration only and are not intended as a definition of the limits of the present invention.

Solvents were purified and dried from a safe purification system. Flash column chromatography was carried out on Silica Gel 60 (230-400 mesh, E. Merck). TLC was performed on pre-coated glass plates of Silica Gel 60 F254 (0.25 mm, E. Merck); detection was executed by spraying with a solution of $Ce(NH_4)_2(NO_3)_6$, $(NH_4)_6Mo_7O_{24}$, and $H_2SO_4$ in water or ninhydrin and acetic acid solution in n-butanol and subsequent heating on a hot plate. Melting points were determined with a Büchi B-540 apparatus and are uncorrected. Optical rotations were measured with a Jasco DIP-370 polarimeter at ~25° C. $^1H$ and $^{13}C$ NMR spectra were recorded with Bruker AMX400 and 500 MHz instruments. Chemical shifts are in ppm from $Me_4Si$, generated from the $CDCl_3$ lock signal at δ 7.24. IR spectra were taken with a Perkin-Elmer Paragon 1000 FT-IR spectrometer. Elemental analyses were measured with a Perkin-Elmer 2400CHN instrument. Mass spectra were obtained with a FAB JMS-700 double focusing mass spectrometer (JEOL, Tokyo, Japan), MALDI Voyager DE-PRO (Applied Biosystem Houston, USA) and ESI Finnigan LCQ mass spectrometer (Thermo Finnigan, San Jose, Calif., United States) in negative mode. Gel-filtration chromatography (Sephadex® G-25 fine) was used in order to achieve purification of the final products.

Example 1

The Furanose, compound 9, refer to FIG. 1A. To a solution of 8 (193 mg, 0.62 mmol) in $CH_2Cl_2$ (2.0 mL) was added pyridine (0.5 mL, 6.18 mmol) at 0° C. under nitrogen. Benzoyl chloride (87 µL, 0.75 mmol) was added subsequently to the mixture in a dropwise manner. After stirring at 0° C. for 2 h, methanesulfonyl chloride (73 µL, 0.94 mmol) was added, the reaction was warmed up to room temperature gradually and kept stirring overnight. The reaction was quenched by addition of $H_2O$ (5 mL). The aqueous layer was extracted with EtOAc (3×10 mL). The combined organic layers were sequentially washed with 1 N HCl, saturated $NaHCO_{3(aq)}$ and brine, dried over $MgSO_4$, filtered, and concentrated in vacuo. The residue was purified by column chromatography (EtOAc/Hex=1/4) to afford 9 (248 mg, 81%) as a white solid.

Example 2

The 2,4-diol, compound 10; refer to FIG. 1B. To a solution of 9 (1.20 g, 2.44 mmol) in a mixed solvent ($CH_2Cl_2$/ ′BuOH=2/1, 18 mL) was added potassium t-butoxide (0.60 g, 5.36 mmol) at 0° C. under nitrogen. After stirring for 16 h, the reaction was neutralized with 0.6 N $H_2SO_{4(aq)}$ (ca. 4.5 mL) and the flask was equipped with a simple distillation head to evaporate $CH_2Cl_2$ and ′BuOH under reduced pressure. 0.6 N $H_2SO_{4(aq)}$ (5 mL) and diglyme (10 mL) were added to the resulting solution and the mixture was kept stirring at 160° C. for another 16 h. After cooling to room temperature, the reaction was neutralized with 3 N $NaOH_{(aq)}$ (2 mL), and the solvent was removed on rotary evaporator under vacuum. Water (10 mL) was added to the residue, and the mixture was extracted with EtOAc (3×10 mL). The combined organic layers were washed with brine, dried over $MgSO_4$, filtered, and concentrated in vacuo. The residue was purified by flash column chromatography (EtOAc/Hex=1/1) to give a white solid, which was further recrystallized via vapor diffusion method to provide 10 (0.32 g, 52%) as colorless crystals.

Example 3

The first alpha-linked disaccharide and first beta-linked disaccharide, compounds 15-alpha and 15-beta; refer to FIG. 1C. A mixture of 14 (0.51 g, 0.95 mmol) and freshly dried 4 Å molecular sieves (1 g) in dichloromethane (5 mL) was stirred at room temperature for 30 min under nitrogen. The reaction flask was cooled to −78° C., anhydrous potassium carbonate (0.26 g, 1.88 mmol) and trichloroacetonitrile (0.95 mL, 9.47 mmol) were sequentially added to the solution, and the mixture was gradually warmed up to room temperature. After stirring for 16 h, the resulting solution was filtered through celite, and the solid was washed with dichloromethane. The filtrate was concentrated in vacuo to afford the crude trichloroacetimidate (0.64 g, 98%, alpha/beta=1/ 1.9 determined by the $^1H$ NMR spectrum), which was directly used without further purification for the ensuing reaction.

A solution of this crude trichloroacetimidate (0.62 g, 0.91 mmol) and 11 (0.49 g, 1.37 mmol) in dichloromethane (11 mL) was added to a reaction flask containing freshly dried 4 Å molecular sieves (2 g) under nitrogen. The mixture was stirred at room temperature for 1 h, and the solution was cooled to −78° C. Trimethylsilyl trifluoromethanesulfonate (25 µL, 0.14 mmol) was added to the reaction flask, the mixture was gradually warmed up to room temperature, and the resulting solution was kept stirring for 6 hours. Triethylamine (50 µL) was added to quench the reaction, and the whole mixture was filtered through celite followed by wash with dichloromethane. The filtrate was concentrated in vacuo to furnish a residue, which was purified by flash column chromatography (EtOAc/Hex=1/4) to yield 15-alpha (0.49 g, 61%) and 15-beta (89 mg, 11%). The alpha-isomer was further recrystallized through vapor diffusion method to get colorless crystals for X-ray single crystal analysis.

Example 4

The second alpha, alpha-linked trisaccharide, compound 23; refer to FIG. 1D. The same procedure as described before for 15-alpha was followed. It took 3 hours to complete the reaction and compound 23 was afforded in 84% yield after flash column chromatography (EtOAc/Hex=1/3).

Example 5

Figure 2:
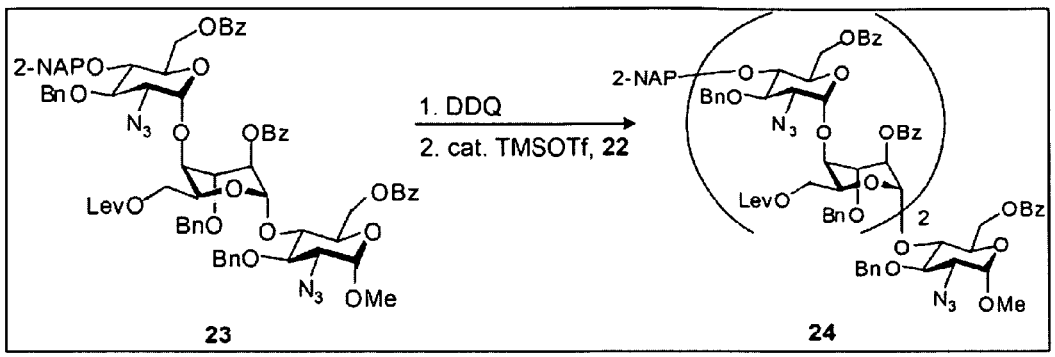
FIGS. 2A, 2B, and 2C show synthesis schemes from Example 5-7.
Figure 2:
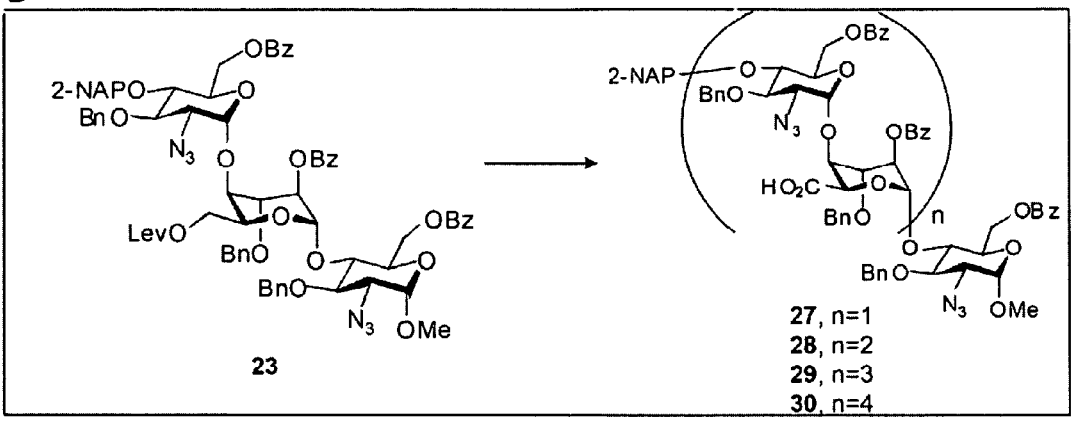
Figure 2:
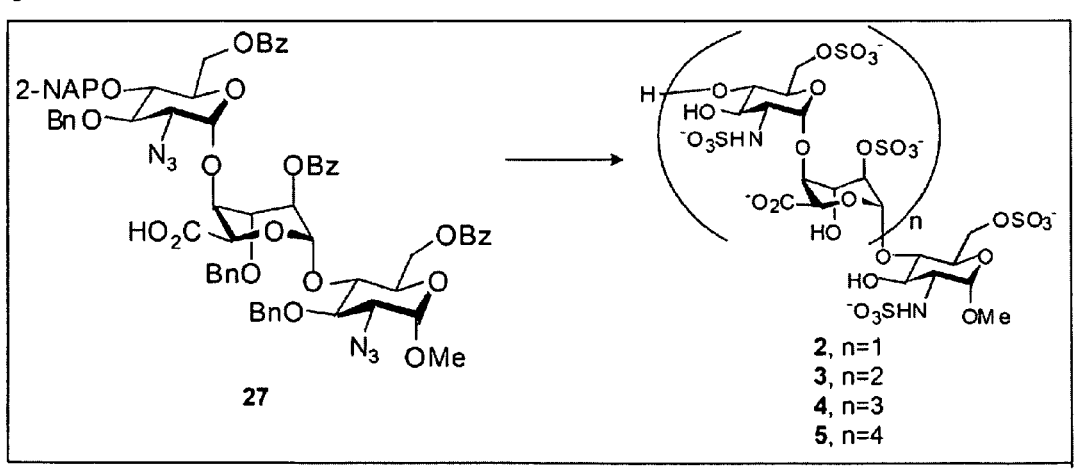

Compound 24; refer to FIG. 2A. To a stirred solution of 23 (0.36 g, 0.26 mmol) in a mixed solvent ($CH_2Cl_2/H_2O$=18/1, 19 mL) was added 2,3-dichloro-5,6-dicyano-1,4-benzoquinone (0.18 g, 0.79 mmol) in three equal portions at halfhour intervals at room temperature. After stirring for 4 h, the reaction was quenched by addition of saturated $NaHCO_{3(aq)}$ (20 mL), and the mixture was extracted with $CH_2Cl_2$ (2×20 mL). The organic layers were consecutively washed with saturated $NaHCO_{3(aq)}$ (2×20 mL) and brine, dried over anhydrous $MgSO_4$, filtered, and concentrated in vacuo. The residue was purified by flash column chromatography (EtOAc/ Hex=1/1.8) to give the 4-OH compound (0.26 g, 80%).

A mixture of this 4-alcohol (0.16 g, 0.13 mmol), the imidate 22 (0.15 g, 0.13 mmol), and freshly dried 4 Å molecular sieves (1 g) in dichloromethane (6 mL) was stirred at room temperature for 1 h under nitrogen. The reaction flask was cooled to −40° C., and trimethylsilyl trifluoromethanesulfonate (5 µL, 0.06 mmol) was added to the reaction mixture. After stirring for 1.5 h, more 22 (0.30 g, 0.26 mmol) in dichloromethane (1 mL) and trimethylsilyl trifluoromethanesulfonate (5 µL, 0.06 mmol) were consecutively added to the solution at the same temperature, and the mixture was stirred for an additional 3 h. The flask was gradually warmed up to room temperature and triethylamine (20 µL) was added to quench the reaction. The mixture was filtered through celite, the solid was washed with dichloromethane, and the filtrate was concentrated in vacuo. The residue was purified by flash column chromatography (EtOAc/Hex=1/2) to provide 24 (0.21 g).

Example 6

Compound 27; refer to FIG. 2B. $H_2NNH_2$/AcOH (33 mg, 0.36 mmol) was added to a solution of compound 23 (100 mg, 72 µmol) in a mixed solvent (ethanol/toluene=2/1, 7.5 mL) at room temperature under nitrogen. After stirring for 2 h, the solvent was removed under reduced pressure, the residue was diluted with $H_2O$ (5 mL), and the mixture was extracted by EtOAc (5 mL×3). The combined organic layers were sequentially washed with saturated $NaHCO_{3(aq)}$ and brine, dried over anhydrous $MgSO_4$, filtered, and concentrated in vacuo to furnish a residue, which was purified by flash column chromatography (EtOAc/Hex=1/3) to afford the primary alcohol.

To a solution of this primary alcohol (44 mg, 34 µmol) in $CH_2Cl_2$ (1.7 mL) was consecutively added $H_2O$ (1.7 mL), 1 M $KBr_{(aq)}$ (34 µL, 34 µmol), TEMPO (5 mg, 34 µmol), 0.5 M $NaHCO_{3(aq)}$ (1.7 mL), and $Bu_4N^+Cl^-$ (19 mg, 68 µmol) at room temperature. The reaction flask was immersed in an ice-bath, and NaOCl (0.22 mL, 3.6 mmol) was added to the mixture which was simultaneously calibrated with 0.5 N $NaOH_{(aq)}$ through micro-syringe to maintain at pH=10. The resulting solution was gradually warmed up to room temperature, and 0.5 N $NaOH_{(aq)}$ was added to keep at the same pH value. After stirring for 3 h, the mixture was extracted with CH$_2$Cl$_2$ (5 mL×3), and the combined organic layers were acidified with 1 N HCl$_{(aq)}$, dried over MgSO$_4$, filtered, and concentrated in vacuo. The residue was purified by flash column chromatography (EtOAc/Hex=1/2) to give 27 (38 mg, 87%).

Compound 28. The same procedure as described before for the trisaccharide 27 was followed. LRMS (MALDI, MNa$^+$) calcd for C$_{112}$H$_{105}$N$_9$O$_{30}$Na 2078.69, found 2078.47.

Compound 29. The same procedure as described before for the trisaccharide 27 was followed. LRMS (MALDI, MNa$^+$) calcd for C$_{152}$H$_{142}$N$_{12}$O$_{42}$Na 2829.92, found 2830.86.

Compound 30. The same procedure as described before for trisaccharide 27 was followed. LRMS (MALDI, MNa$^+$) calcd for C$_{192}$H$_{179}$N$_{15}$O$_{54}$Na 3581.16, found 3581.96.

Example 7

Compound 2; Refer to FIG. 2C.

(1) Debenzoylation. Sodium methoxide (6.0 mg, 0.11 mmol) was added to a solution of 27 (36 mg, 28 µmol) in methanol (0.6 mL) at room temperature under nitrogen. The mixture was kept stirring overnight, and the reaction solution was neutralized by Amberlite-120 acidic resin. The resulting mixture was filtered through paper, and the filtrate was concentrated in vacuo to yield the crude triol, which was directly used for next step (2) O-Sulfonation. A solution of this crude triol and sulfur trioxide-triethylamine complex (0.22 g, 1.2 mmol) in DMF (0.6 mL) was stirred at 50° C. under nitrogen overnight. The reaction flask was cooled down to room temperature, a solution of NaHCO$_3$ (0.42 g) in H$_2$O (5 mL) was added to the mixture, and the mixture was kept stirring for another 16 h. The solvent was coevaporated with ethanol under reduced pressure, and a mixed solvent of CH$_2$Cl$_2$/MeOH (1/1, 10 mL) was added to the residue. The mixture was filtered through paper, and the filtrate was concentrated in vacuo to give a syrup that was dissolved in a mixed solvent CH$_2$Cl$_2$/MeOH (4/1, 10 mL). Repeating of the filtration and concentration steps led to the crude tri-O-sulfonated derivative, which was used for next reaction without further purification. LRMS (ESI negative mode) calcd for [M−2H+Na]$^-$ 1253.22, found 1253.28.

(3) Hydrogenolysis. A solution of this crude compound in a mixed solvent 1:9 H$_2$O/MeOH (1/9, 4 mL) was hydrogenated in the presence of 10% Pd/C (70 mg) under 50 psi pressure at room temperature. After 2 d, the mixture was filtered through celite, and the filtrate was concentrated in vacuo. The same procedure was repeated again until no signals of aryl groups could be detected by $^1$H NMR spectrum.

(4) N-sulfonation. The above amino-alcohol was dissolved in water (3 mL), and the solution was adjusted to pH=9.5 through addition of 2 N NaOH$_{(aq)}$. Sulfur trioxide-pyridine complex (0.17 g, 1.0 mmol) was added in five equal portions at half-hour intervals at room temperature, and the pH value was maintained at 9.5 via calibration of 2 N NaOH$_{(aq)}$. After stirring for 3 h, the reaction mixture was concentrated in vacuo, and the residue was purified by column chromatography on Sephadex G-25 using 0.2 N NaCl$_{(aq)}$ as an eluent. The crude product portion was lyophilized followed by desalting through a Sephadex G-25 column eluted with water to give compound 2 (10 mg, 36%) as a white solid. LRMS (ESI negative mode) calcd for [M−2H+Na]$^-$ 950.95, found 951.17; calcd for [M−3H+2Na]$^-$ 972.94, found 973.25.

Compound 3.

The same protocol as described before for the trisaccharide 2 was followed to obtain the pentasaccharide 3 in 21% overall yield. (1) Debenzoylation. HRMS (MALDI, MNa$^+$) calcd for C$_{77}$H$_{85}$N$_9$O$_{25}$Na 1558.5533, found 1558.5508. (2) O-Sulfonation. LRMS (ESI negative mode) calcd for [M−5H+4Na]$^-$ 2022.27, found 2021.00. (3) Hydrogenolysis and N-Sulfonation.

Compound 4.

The same protocol as described before for the trisaccharide 2 was followed to obtain the heptasaccharide 4 in 8% overall yield. (1) Debenzoylation. LRMS (MALDI, MNa$^+$) calcd for C$_{103}$H$_{114}$N$_{12}$O$_{35}$Na 2101.74, found 2101.92. (2) O-Sulfonation. LRMS (ESI negative mode) calcd for [M−8H+7Na]$^-$ 2791.32, found 2792.36. (3) Hydrogenolysis and N-Sulfonation. LRMS (ESI negative mode) calcd for [M−3H+2Na]$^-$ 2126.88, found 2127.00; calcd for [M−9H+8Na]$^-$ 2258.77, found 2259.00.

Compound 5.

The same protocol as described before for the trisaccharide 2 was followed to obtain the nonasaccharide 5 in 7% overall yield. (1) Debenzoylation. LRMS (MALDI, MNa$^+$) calcd for C$_{129}$H$_{143}$N$_{15}$O$_{45}$Na 2644.93, found 2644.44. (2) O-Sulfonation. LRMS (ESI negative mode) calcd for [M−8H+7Na]$^-$ 3494.41, found 3494.00; calcd for [M−10H+9Na]$^-$ 3538.38, found 3538.00. (3) Hydrogenolysis and N-Sulfonation.

We claim:

1. An orthogonally protected disaccharide building block of formula (I):

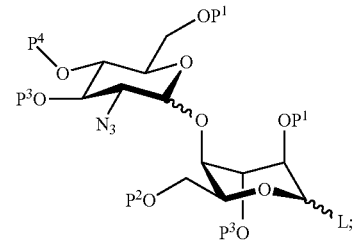

wherein L is a leaving group O-trichloroacetimidyl, P$^1$, P$^2$, P$^3$ and P$^4$ are hydroxyl protecting groups, and of them P$^1$ is an ester-type protecting group selected from the group consisting of acyl and benzoyl (Bz), P$^2$ is selected from the group consisting of levulinyl (Lev), acyl and acetyl (Ac), P$^3$ is benzyl (Bn) or substituted benzyl, and P$^4$ is selected from the group consisting of naphthylmethyl (NAP), substituted naphthylmethyl, p-methoxybenzyl and substituted p-methoxybenzyl, and wherein the wavy line represents an α- or β-linkage.

2. The disaccharide building block of claim 1 having formula:

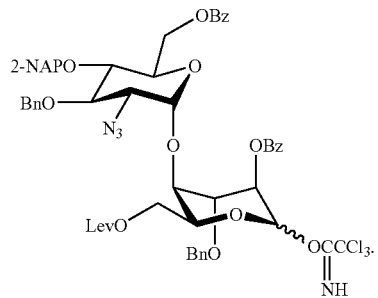

3. The disaccharide building block of claim 1 having formula:

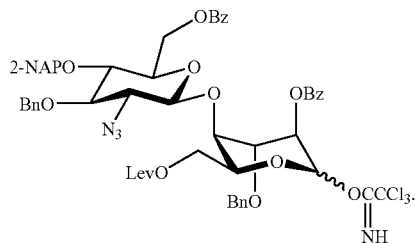

4. The disaccharide building block of claim 1 having formula:

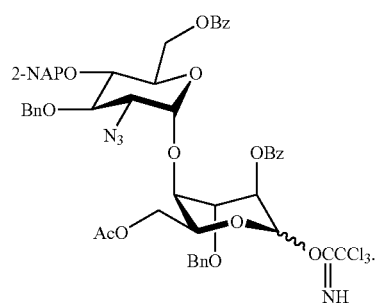

5. The disaccharide building block of claim 1 having formula:

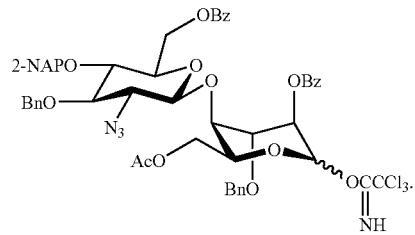

6. A method for synthesizing an orthogonally protected disaccharide building block of formula (I) according to claim 1 comprising the steps of:

a) reacting the L-idopyranosyl sugar of formula (III) with 2-Azido-6-O-benzoyl-3-O-benzyl-2-deoxy-4-O-(2-naphthylmethyl)D-glucopyranosyl trichloroacetimidate of formula (IV) in the presence of a catalyst to produce a disaccharide intermediate of formula(VII):

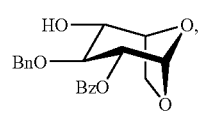

(III)

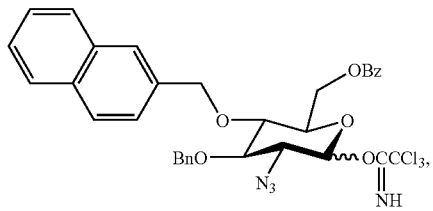

(IV)

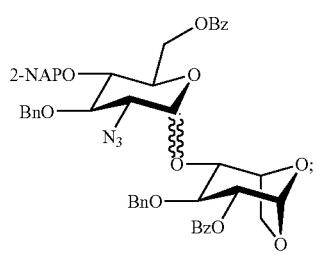

(VII)

b) contacting the product of formula (VII) from step (a) With acetic anhydride in the presence of a catalyst to produce an 1,6-diacetylated product of formula (VIII):

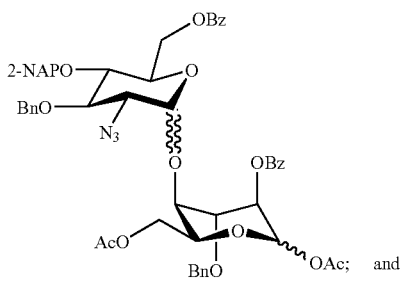

(VIII)

c) performing selective O1-deacetylation by contacting the 1,6-diacetylated product of formula (VIII) from step (b) with ammonia in the presence of an organic solvent to produce an O1-deacetylated product, and contacting the O1-deacetylated product with trichloroacetonitrile ($CCl_3CN$) in the presence of an organic base to produce an orthogonally protected disaccharide building block of formula (I) according to claim 1, or d) selectively performing deacetylation of the product of formula (VIII) by contacting it with an acid to produce an 1,6-diol product of formula (IX) and contacting the 1,6-diol product of formula (IX) with $(Lev)_2O$ to produce an 1,6-dilevulinylated product of formula (X):

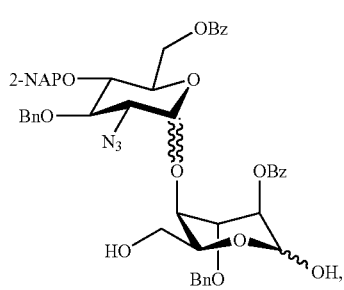

(IX)

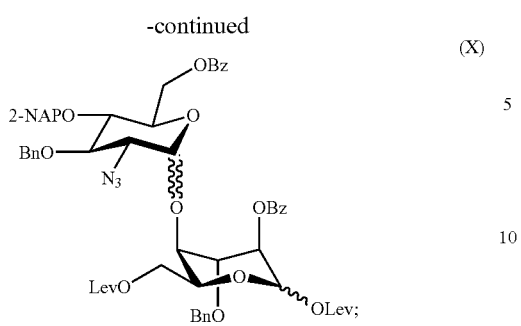

(X)

e) contacting the product of formula (X) with a hydrolytic agent to selectively remove one levulinyl group to produce a product of formula (XI):

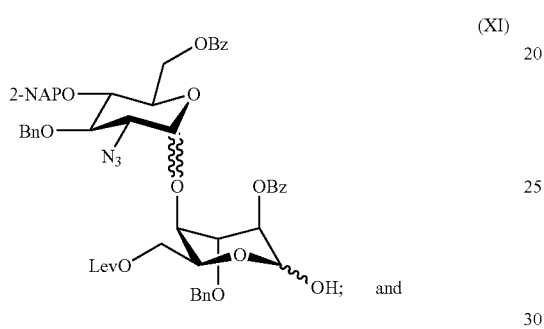

(XI)

f) reacting the product of formula (XI) with trichloroacetonitrile (Cl₃CCN) to produce an orthogonally protected disaccharide building block of formula (I) according to claim 1, wherein $P^2$ is Lev.

7. The method of claim 6, wherein the catalyst in step (a) is trimethylsilyl trifluoromethanesulfonate (TMSOTf).

8. The method of claim 6, wherein the organic base in step (c) is 1,8-diazabicycloundec-7-ene (DBU).

9. The method of claim 6, wherein the hydrolytic agent in step (e) is hydrazine.

10. The method of claim 6, further comprising, prior to the reacting step (a), a process for synthesizing a L-idopyranosyl sugar of formula (III):

(III)

which comprises the steps of:

i) reacting 5,6-diol of formula (XII) with a benzoylation agent and a mesylation agent in one step to produce a furanose of formula (XIII):

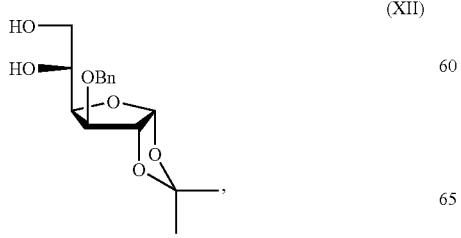

(XII)

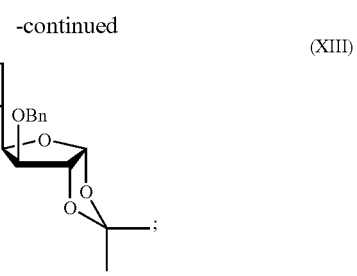

(XIII)

ii) reacting the product of formula (XIII) from step (i) with BuOK to produce an 1,6-anhydro-β-L-idopyranosyl 2,4-diol product of formula (XIV):

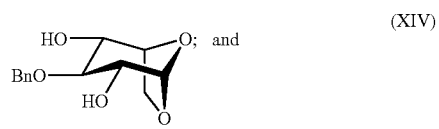

(XIV)

iii) regioselectively benzoylating the product of formula (XIV) by contacting it with a benzoylation agent in the presence of an organic base to produce a L-idopyranosyl sugar of formula (III):

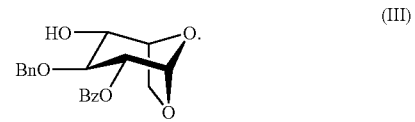

(III)

11. The method of claim 6 further comprising, prior to step (a), a process for synthesizing 2-Azido-6-O-benzoyl-3-O-benzyl-2-deoxy-4-O-(2-naphthylmethyl) D-glucopyranosyl trichloroacenmidate of formula (IV):

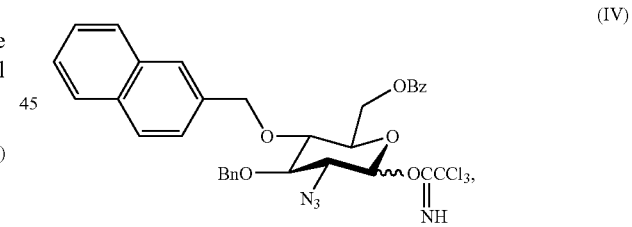

(IV)

which includes the steps of:
i) providing glucosamine of formula:

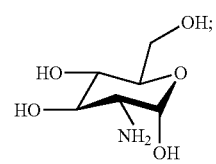

ii) transforming glucosamine into 2-Azido-2-deoxy4,6-O-(2-naphthylmethylene)-D-glucopyranose of formula (XV) by a process comprising the steps of:
(a) performing an amino-azido conversion at C2 by contacting the glucosamine with trifluoromethanesulfonyl azide (TfN3) in the presence of a catalyst to produce an azido product; and (b) performing a 4,6-O-naphthylidenation by contacting the azido product with 2-naphthaldehyde dimethyl acetal in the presence of a catalyst to produce a product of formula (XV):

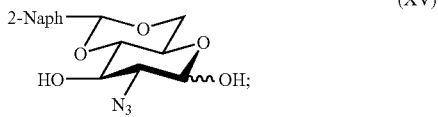

iii) performing regioselective O1-benzoylation of the product of formula (XV) from step (ii) by contacting it with 1-N-(benzoyloxy)benzotriazole (BzOBT) in the presence of an organic base at room temperature to produce 2-Azido-2-deoxy-4,6-O-(2-naphthylmethylidene)-β-D-glucopyranosyl benzoate of formula (XVI):

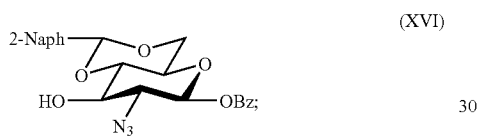

iv) performing O3-benzylation of the product of formula (XVI) from step (iii) by reacting it with a benzylation agent to produce 2-Azido-3-O-benzyl-2-deoxy-4,6-O-(2-naphthylmethylidene)-β-D-glucopyranosyl benzoate of formula (XVII):

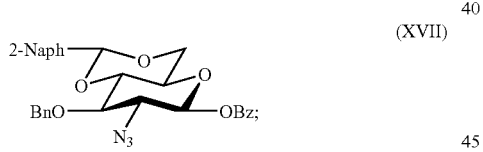

v) contacting the product of formula (XVII) from step (iv) with a hydrogenolysis-capable reductant in the presence of a catalyst to open the ring to produce 2-Azido-3-O-benzyl-2-deoxy-4-O-(2-naphthylmethyl)-glucopyranosyl benzoate of formula (XVIII):

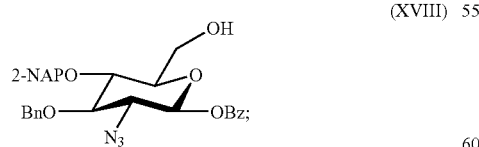

vi) performing O6-benzoylation of the product of formula (XVIII) from step (v) by reacting with a benzoylation agent to produce 2-Azido-6-O-benzoyl-3-O-benzyl-2-deoxy-4-O-(2-naphthylmethyl)-β-D-glucopyranosyl benzoate of formula (XIX):

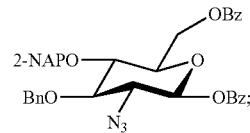

vii) performing selective debenzoylation of the product of formula (XIX) from step (vi) by contacting it with NH$_3$ (g) in the presence of an organic solvent to produce 2-Azido-6-O-benzoyl-3-O-benzyl-2-deoxy-4-O-(2-naphthylmethyl)-D-glucopyranose of the formula (XX):

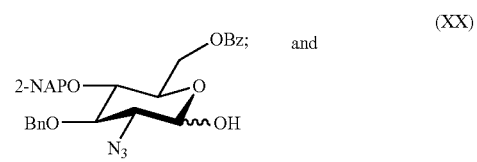

viii) reacting the product of formula (XX) from step (vii) with trichloroacetonitrile (CCl$_3$CN) in the presence of an organic base to produce 2-Azido-6-O-benzoyl-3-O-benzyl-2-deoxy-4-O-(2-naphthylrnethyl) D-glucopyranosyl trichloroacetimidate of formula (IV):

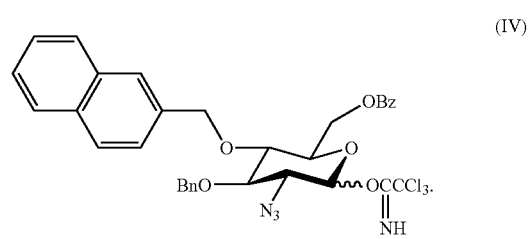

12. A method for synthesizing a heparin oligosaccharide of formula:

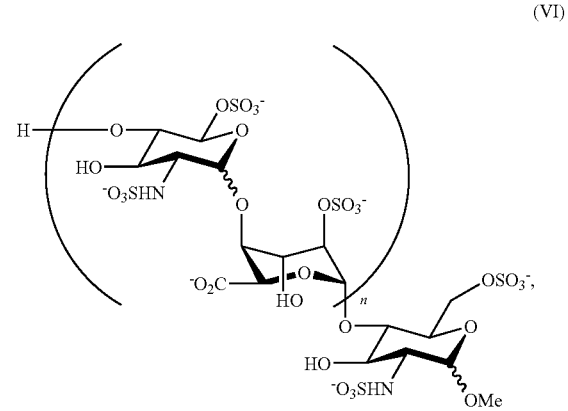

wherein n is an integer ranging from 1 to 100 and the wavy line represents an α- or β-linkage, comprising the steps of:
a) contacting a starting unit of formula (II) with an orthogonally protected disaccharide building block of formula (I) in the presence of a catalyst to produce a trisaccharide of formula (V):

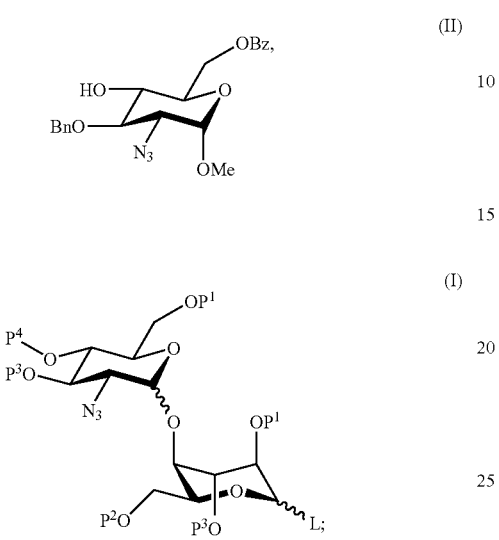

wherein L is the leaving group O-trichloroacetimidyl, $P^1, P^2, P^3$ and $P^4$ are hydroxyl protecting groups, and of them $P^1$ is an ester-type protecting group selected from the group consisting of acyl and benzoyl (Bz), $P^2$ is levulinyl (Lev), $P^3$ is benzyl (Bn) or substituted benzyl, and $P^4$ is selected from the group consisting of naphthylmethyl (NAP), substituted naphthylmethyl, p-methoxybenzyl and substituted p-methoxybenzyl, and wherein the wavy line represents an α-or β-linkage,

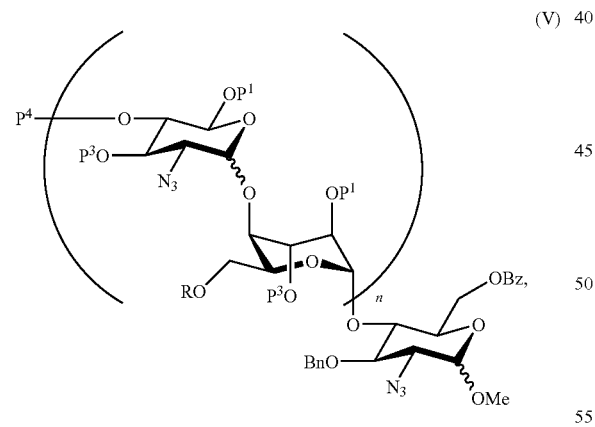

wherein n=1, R=Lev;
b) optionally performing m cycles of chain elongation reaction on the product from the prior step (a) or cycle, with each cycle comprising the steps of:
 (i) selectively oxidizing the product from the prior step (a) or cycle with an oxidizing agent to produce a product of formula (V), wherein $P^4$=H, n=m; and
 (ii) glycosylating the product from step (b)(i) by adding a disaccharide building block of formula (I) to produce a product of formula (V), wherein n=m+1 and m is an integer ranging from 1 to 99;

c) cleaving the Lev group by contacting the product from step (b)(ii) with a hydrolysis reagent to produce a primary alcohol of formula (VI):

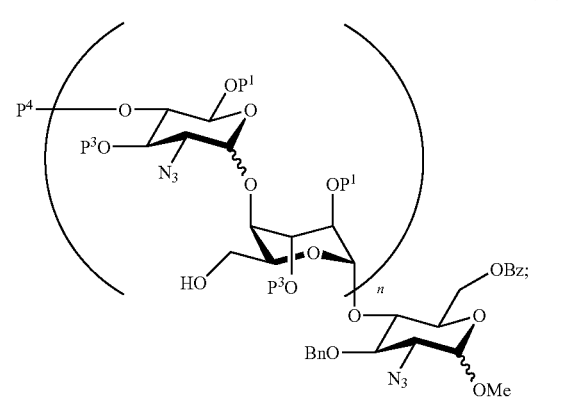

d) selectively reacting the primary hydroxyls of the product of formula (VI) from step (c) by contacting it with an oxidizing agent to obtain an acid of formula:

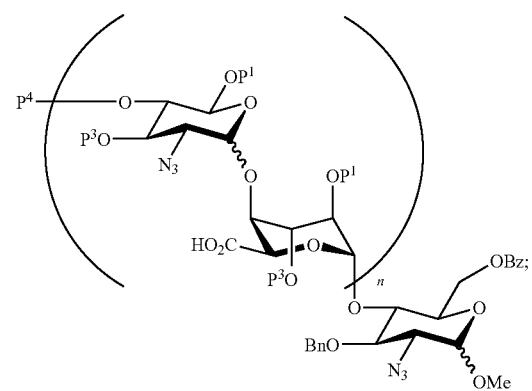

e) reacting the product from step (d) with an alkoxide to remove the $P^1$ and benzoyl protecting groups to produce a product of formula:

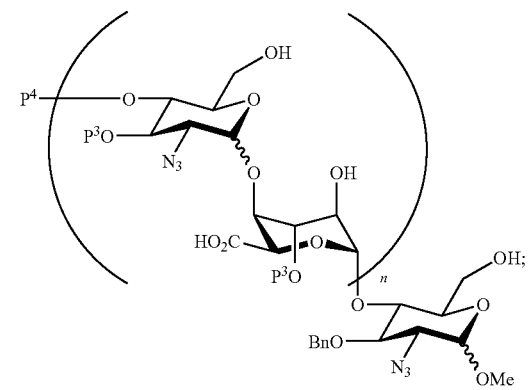

f) performing O-sulfonation by reacting the product from step (e) with a sulfonating agent to produce a sulfonated product of formula:

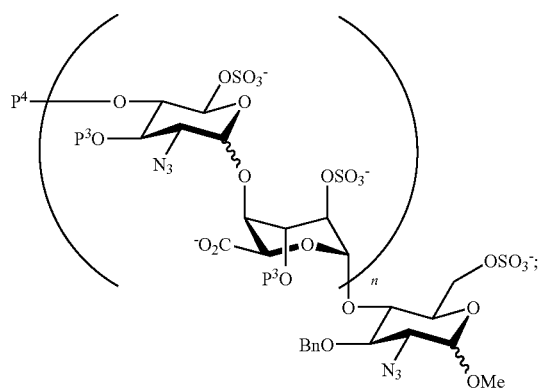

g) performing hydrogenolysis and azide reduction by reacting the product from step (f) with $H_2$ in the presence of a hydrogenolysis/hydrogenation catalytic agent to produce a D-glucopyranoside product of formula:

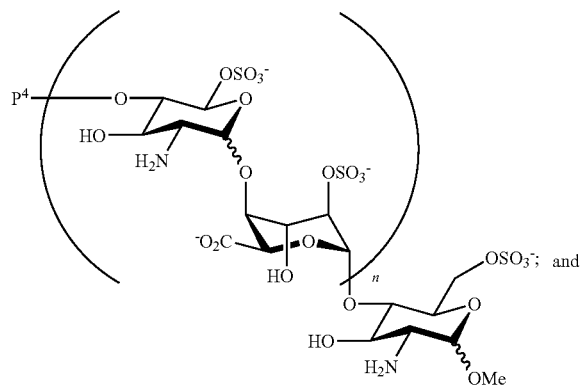

h) performing N-sulfonation by reacting the product of step (g) with a sulfonating agent to produce the heparin oligosaccharide of formula (VI).

13. The method of claim 12, wherein the chain elongation reaction is performed 2, 3, or 4 cycles.

14. The method of claim 12, wherein the oxidizing agent in step (b) is 2,3-dichloro-5,6-dicyano-1,4-benzoquinone (DDQ).

15. The method of claim 12, wherein the hydrolytic agent in step (c) is hydrazine ($N_2H_4$).

16. The method of claim 12, wherein the oxidizing agent in step (d) is sodium hypochlorite (NaOCl), an agent that oxidizes the primary hydroxyl groups present to carboxyl groups.

17. The method of claim 12, wherein the alkoxide in step (e) is sodium methoxide (NaOMe).

18. The method of claim 12, wherein the sulfonating agent in the step (f) is sulfur trioxide-triethylamine complex ($SO_3$-$Et_3N$).

19. The method of claim 12, wherein the hydrogenolysis/hydronenation in step (g) is carried out with palladium on carbon (Pd/C) as the catalytic agent.

20. The method of claim 12, wherein the sulfonating agent in the step (h) is sulfur trioxide-pyridine complex ($SO_3$-Pyr).

* * * * *